United States Patent
Stout et al.

(10) Patent No.: US 10,485,752 B2
(45) Date of Patent: Nov. 26, 2019

(54) SKIN REJUVENATION AND DEFENSE SYSTEMS AND METHODS

(71) Applicant: Maple Mountain Group, Inc., Springville, UT (US)

(72) Inventors: Holly Stone Stout, Saratoga Springs, UT (US); Keith Alan Murphy, Salem, UT (US)

(73) Assignee: Maple Mountain Group, Inc., Springville, UT (US)

( * ) Notice: Subject to any disclaimer, the term of this patent is extended or adjusted under 35 U.S.C. 154(b) by 27 days.

(21) Appl. No.: 15/895,221

(22) Filed: Feb. 13, 2018

(65) Prior Publication Data

US 2018/0169002 A1    Jun. 21, 2018

Related U.S. Application Data

(62) Division of application No. 15/240,924, filed on Aug. 18, 2016, now Pat. No. 9,925,137.

(60) Provisional application No. 62/373,913, filed on Aug. 11, 2016, provisional application No. 62/207,235, filed on Aug. 19, 2015.

(51) Int. Cl.
| | | |
|---|---|---|
| A61K 8/97 | (2017.01) | |
| A61K 8/99 | (2017.01) | |
| A61K 8/73 | (2006.01) | |
| A61Q 19/08 | (2006.01) | |
| A61Q 19/00 | (2006.01) | |
| A61K 8/34 | (2006.01) | |
| A61K 8/92 | (2006.01) | |
| A61K 8/42 | (2006.01) | |
| A61K 8/9706 | (2017.01) | |
| A61K 8/60 | (2006.01) | |
| A61K 8/70 | (2006.01) | |
| A61K 8/31 | (2006.01) | |
| A61K 8/9794 | (2017.01) | |

(52) U.S. Cl.
CPC ............ *A61K 8/9794* (2017.08); *A61K 8/315* (2013.01); *A61K 8/345* (2013.01); *A61K 8/42* (2013.01); *A61K 8/60* (2013.01); *A61K 8/602* (2013.01); *A61K 8/70* (2013.01); *A61K 8/73* (2013.01); *A61K 8/922* (2013.01); *A61K 8/97* (2013.01); *A61K 8/9706* (2017.08); *A61K 8/99* (2013.01); *A61Q 19/007* (2013.01); *A61Q 19/08* (2013.01); *A61K 2800/884* (2013.01)

(58) Field of Classification Search
CPC .............................................. A61K 2800/884
See application file for complete search history.

(56) References Cited

U.S. PATENT DOCUMENTS

| | | | | |
|---|---|---|---|---|
| 5,885,564 | A | * | 3/1999 | Zastrow ................... A61K 8/22 424/195.16 |
| 9,925,137 | B2 | | 3/2018 | Stout et al. |
| 2010/0316720 | A1 | | 12/2010 | Stutz |
| 2011/0171332 | A1 | | 7/2011 | Soudant |
| 2013/0045290 | A1 | | 2/2013 | Somerville |
| 2013/0287714 | A1 | | 10/2013 | Gohla |
| 2014/0271505 | A1 | * | 9/2014 | Claiborne ................ A61K 8/64 424/59 |
| 2015/0057372 | A1 | | 2/2015 | Ellis |

FOREIGN PATENT DOCUMENTS

FR    3003166    9/2014

OTHER PUBLICATIONS

Mibelle "Snow algae powder," Oct. 2014; http://www.in-cosmetics.com/_novadocuments/65177?v=635489773889800000.
Schmid et al. "Rejuvenating effect of snow algae analysed," Personal Care, Apr. 2014.
"Mama Mio—a review," Mar. 30, 2012; https://beautywithattitude.wordpress.com/2012/03/30/mama-mio-a-review/.
Ipatenco "What are the benefits of aloe vera water?" last updated Apr. 23, 2015; http://www.livestrong.com/article/295284-what-are-the-benefits-of-aloe-vera-water/.
van Laere et al. "Inulin metabolism in dicots: chicory as a model system," Plant, Cell and Environment 25:803-813, 2002.
von Oppen-Bezalel "Leucojum aestivum bulb extract for antiaging benefits," Cosmetics & Toiletries magazine.
U.S. Appl. No. 15/240,924, Jun. 5, 2017, Office Action.
U.S. Appl. No. 15/240,924, Nov. 13, 2017, Notice of Allowance.

* cited by examiner

*Primary Examiner* — David J Blanchard
*Assistant Examiner* — Alissa Prosser
(74) *Attorney, Agent, or Firm* — Workman Nydegger

(57) ABSTRACT

A skin defense system and a skin rejuvenation and defense system. The skin rejuvenation and defense system includes a skin rejuvenation application and a skin defense application that work together synergistically to rejuvenate and defend the skin from environmental insults that can accelerate the aging process and deprive the skin of its vitality. The skin rejuvenation application invigorates, oxygenates, and detoxifies the skin. After the skin has been opened up and made receptive by the skin rejuvenation application, the skin defense application absorbs into the skin to deeply moisturize and revitalize the skin. In addition to moisturizers, emollients, and similar ingredients that improve health and appearance of the skin, the skin defense application includes ingredients that can, for instance, reverse and protect the skin from damage caused by pollutants (e.g., pollutants up to 2.5 micrometers) and pre- and pro-biotics that promote the growth and development of beneficial skin flora.

19 Claims, No Drawings

SKIN REJUVENATION AND DEFENSE SYSTEMS AND METHODS

CROSS REFERENCE TO RELATED APPLICATIONS

This application is a Divisional of U.S. patent application Ser. No. 15/240,924, entitled "Skin Rejuvenation and Defense System," filed 18 Aug. 2016, which claims the benefit of and priority to (1) U.S. Prov. Pat. App. Ser. No. 62/373,913 entitled "Skin Rejuvenation and Defense System," filed 11 Aug. 2016 and (2) U.S. Prov. Pat. App. Ser. No. 62/207,235 entitled "Skin Rejuvenation and Defense System," filed 19 Aug. 2015. Each of the foregoing documents is incorporated by reference herein in their entirety.

BACKGROUND

Our skin suffers a host of insults every day—age related damage, UV damage, pollution, oxidative damage, etc. In addition to being enjoyable, there are a multitude of benefits to your skin and your overall health that can be gained from daily skin care.

Facials, face packs, aromatherapy facials and massage with facial creams and other remedies help deep cleanse the skin, removing toxins caused by pollution, grease and dirt found in your everyday environment. Such facials help to reduce an overabundance of sebum, which is a natural substance that moisturizes and lubricates the skin. Overproduction of sebum can cause skin problems, including blackheads and acne. Cleansing facials open the pores of the skin, remove dead skin and toxins from the face, and clean the surface of the skin through exfoliation that tightens and firms the skin.

Facial treatments help to improve and restore circulation to facial skin layers, increasing the flow of oxygen-enriched blood to skin cells. This rush of blood to the skin gives your skin a healthy glow and plumps skin cells with vital nutrients and water, which reduce the appearance of wrinkled and dry skin. Nutrients like blood, vitamins and minerals found in the blood, along with adequate hydration, help develop and maintain new skin cells, essential for a youthful, healthy appearance.

In addition to the obvious outward benefits, facial treatments feel good, offering soothing relaxation. Daily facial care increases circulation and the flow of blood, and includes a variety of creams, aromatherapy and oils that moisturize the skin, smell good, and relieve stress as well as encourage peace of mind and contentment.

SUMMARY

Disclosed herein is a skin rejuvenation and/or defense system. The skin defense system includes a skin defense application, and the skin rejuvenation and defense system includes a skin rejuvenation application and a skin defense application that work together synergistically to rejuvenate and defend the skin from environmental insults that can, for instance, accelerate the aging process and deprive the skin of its vitality. The skin rejuvenation application can be formulated to, for example, invigorate, oxygenate, and detoxify the skin. The skin defense application can be formulated to, for example, absorb into the skin to deeply moisturize and revitalize the skin after the skin has been opened up and made receptive by the skin rejuvenation application. In addition to moisturizers, emollients, and similar ingredients that improve health and appearance of the skin, the skin defense application includes ingredients that can, for instance, reverse and protect the skin from damage caused by pollutants (e.g., Particulate Matter up to 2.5 micrometers in size, or "pm2.5" pollutants) and pre- and pro-biotics that promote the growth and development of beneficial skin flora.

In an embodiment, a skin rejuvenation and defense system is disclosed. The skin rejuvenation and defense system includes: (A) skin rejuvenation application that includes a (i) *Coenochloris signiensis* (a.k.a. Snow Algae) preparation, (ii) a *Leucojum aestivum* bulb extract (commercially available as IBR-Snowflake® from IBR, Israel), (iii) perfluorocarbons (e.g., perfluorohexane, perfluorodecalin, and pentafluoropropane (commercially available as FiFlow® BB61 from The Innovation Company®, France and/or provided in or as (components of) Ox3™ (by Mōdere™, Springville, Utah)), and/or (iv) water; and (B) a skin defense application that includes (i) *Taraxacum officinale* (a.k.a. dandelion) extract (commercially available as Apolluskin® from Silab, France), (ii) a pre-/pro-biotic complex, comprising alpha-glucan oligosaccharide (or α-glucooligosaccharides), β-fructooligosaccharides (e.g., (as or obtained from) *Smallanthus sonchifolius* (syn.: *Polymnia edulis, P. sonchifolia*) and/or *Pachyrhizus erosus* (a.k.a. jicama) root juice), maltodextrin, and *Lactobacillus* sp. (e.g., *Lactobacillus casei, L. acidophilus*) probiotic bacteria (commercially available as Ecoskin® from Solabia Group, France), (iii) an emulsifier, (iv) a moisturizer, and/or (v) water. The skin rejuvenation application can be configured to be applied to a skin surface, left on for a selected period of time, and then rinsed off. The skin defense application can be configured to be applied to the skin surface after removal of the skin rejuvenation application and to be left on the skin.

In an embodiment, a skin rejuvenation and defense system can comprise: a skin rejuvenation application that includes a Snow Algae preparation (*Coenochloris signiensis*), IBR Snowflake® (*Leucojum aestivum* bulb extract), FiFlow® BB61 (perfluorohexane, perfluorodecalin, and pentafluoropropane), and/or water; and/or a skin defense application that includes Apolluskin® (*Taraxacum officinale* (dandelion) extract), Ecoskin® (alpha-glucan oligosaccharide, *Polymnia sonchifolia* root juice, maltodextrin, *Lactobacillus*), an emulsifier, a moisturizer, and/or water.

In an embodiment, the selected period of time can range from about 30 seconds to about 10 minutes. The skin rejuvenation application can be packaged in a substantially airtight container. The emulsifier and the moisturizer of the skin defense application can comprise butylene glycol, shea butter, hydroxyethyl urea, propanediol, Lecigel™ (sodium acrylates copolymer and lecithin), and/or Emulium® mellifera (Emulsifier 75C) (polyglyceryl-6 distearate, jojoba esters, polyglyceryl-3 beeswax, cetyl alcohol).

In an embodiment, the skin defense application includes about 1-5 weight % (wt %) of the Apolluskin®, about 1-5 wt % of the Ecoskin®, about 3-10 wt % of the butylene glycol, about 0.1-3 wt % of the shea butter, about 0.1-3 wt % of the hydroxyethyl urea, about 0.1-3 wt % of the propanediol, about 0.1-3 wt % of the Lecigel™ (sodium acrylates copolymer and lecithin), about 1-5 wt % of the Emulium® mellifera, and/or about 60-80 wt % water.

In an embodiment, the skin rejuvenation application can comprise (a blend or mixture of) water, Carbopol® Aqua SF-1 (Acrylates Copolymer), DL-Panthenol 50% liquid (panthenol, water), hydroxyethyl urea, pentylene glycol, decyl glucoside, Iselux® SFS (water, sodium lauroyl methyl isethionate, cocamidopropyl betaine, sodium methyl oleoyl, taurate, sodium cocoyl isethionate,), IBR Snowflake® (water, *Leucojum aestivum* bulb extract), Snow Algae preparation (maltodextrin, water, *Coenochloris signiensis* extract, lecithin), propanediol, xanthan gum, AMP-Ultra™ PC 2000 (aminomethyl propanol, water), ethoxydiglycol, polysorbate 20, Botanistat PF-64™ (Phenoxyethanol, Caprylyl Glycol, Ethylhexylglycerin, Hexylene Glycol), aromatic mandarin ginger lily extract blend (caprylic/capric triglyceride, *Citrus aurantium dulcis* (orange) fruit extract, *Citrus aurantium dulcis* (orange) peel extract, *Lavandula angustifolia* (Lavender) flower/leaf/stem extract, *Elettaria cardamomum* seed extract, *Gardenia taitensis* flower extract, *Prunus armeniaca* (apricot) fruit extract, *Pyrus malus* (apple) fruit extract, *Hibiscus abelmoschus* seed extract, *Eugenia caryophyllus* (clove) flower extract, *Vanilla planifolia* fruit extract, *Jasminum officinale* (jasmine) flower/leaf extract, *Hedychium spicatum* extract, *Plumeria rubra* flower extract), and/or Fiflow® BB61 (perfluorohexane, perfluorodecalin, pentafluoropropane).

In an embodiment, the skin defense application can comprise (a blend or mixture of) water, Dissolvine® GL-47-S (Tetrasodium Glutamate Diacetate, Carbopol® Utrez 21, SymSave® H, Butylene Glycol, Emulium® meliffera (Emulsifier 75C) (Polyglyceryl-6 Distearate, Jojoba Esters, Polyglyceryl-3 Beeswax, Cetyl Alcohol), Fancol Karite Butter (*Butyrospermum parkii* (Shea) Butter), Botanisil™ DM-85 (Dimethicone), Symocide® PS (Phenoxyethanol, Decylene Glycol, 1,2-Hexanediol), Zemea® (Propanediol), Apolluskin® (*Taraxacum officinale* (Dandelion) Root Extract), SymDiol® 68 (1,2-Hexanediol, Caprylyl Glycol), Nalidone® (Sodium PCA), Vitamin E Blend, Ecoskin® (Alpha-Glucan Oligosaccharide), Floraesters K-20W® (Hydrolyzed Jojoba Esters, water), Allantoin, Hydrovance® (Hydroxyethyl Urea), Aromatic Ginger Yuzu Extract Blend, Lecigel™ (Sodium Acrylates Copolymer and Lecithin), and/or, optionally Citric Acid (50% Solution) and/or Sodium Hydroxide (50% Solution) (e.g., to a pH of about 5.75-6.25).

In another embodiment, a method for skin rejuvenation and defense is disclosed. The method for skin rejuvenation and defense includes (1) applying the skin rejuvenation application to a selected skin area, (2) leaving the skin rejuvenation application in contact with the skin for a selected period of time, (3) rinsing the skin rejuvenation application off of the skin, and/or (4) applying the skin defense application to the selected skin area (e.g., after applying, leaving, and/or rinsing the skin rejuvenation application). Some embodiments can include applying (and rinsing) a skin cleanser (e.g., wash, soap, scrub, exfoliant, etc.) to (and from) the selected skin area (e.g., prior to application of the skin rejuvenation application). In one aspect, the skin rejuvenation application and the skin defense application may be applied to the selected skin area at night (e.g., before going to bed). In one embodiment, the method further includes reapplying the skin defense application to the selected skin are at least one additional time in a following 24 hour period (e.g., within 6-10 hours or after waking in the morning).

In an embodiment, a method for skin rejuvenation and defense can comprise applying a skin rejuvenation application to a selected skin area, leaving the skin rejuvenation application in contact with the skin for a selected period of time, rinsing the skin rejuvenation application off of the skin, and/or applying a skin defense application to the selected skin area. The skin rejuvenation application can include a Snow Algae (*Coenochloris signiensis*) preparation, IBR Snowflake® (*Leucojum aestivum* bulb extract), FiFlow® BB61 (perfluorohexane, perfluorodecalin, and pentafluoropropane), and/or water. The skin defense application can includes Apolluskin (*Taraxacum officinale* (dandelion) extract), Ecoskin® (alpha-glucan oligosaccharide, *Polymnia sonchifolia* root juice, maltodextrin, *Lactobacillus*), an emulsifier, a moisturizer, and/or water.

In an embodiment, the skin rejuvenation application and/or the skin defense application can be applied to the selected skin area at night, and/or the method can (further) comprise (re)applying the skin defense application to the selected skin are at least one additional time in a following 24 hour period. The skin defense application can be (re)applied to the selected skin area at least once within a period of 6-10 hours after the first application. The selected skin area can include at least a portion of a human face. The selected skin area can include skin of a face and neck area.

In an embodiment, the selected period of time that the skin rejuvenation application is in contact with the selected skin area can range from about 30 seconds to about 10 minutes. The method can include dispensing an amount of the skin rejuvenation application sufficient for a single application from an airtight container.

Embodiments of the present disclosure can also (or alternatively) include or be formulated into other skin care product forms and/or treatment methods (e.g., for face (e.g., eye, cheek, chin, mouth, ear, forehead, or other area(s)), neck, and/or body) utilizing the disclosed ingredients and/or technologies. Such embodiments can comprise or be in liquid, solid, semi-solid, or other form, or mixture thereof, including but not limited to creams, gels, lotions, pastes, sprays, mists, aerosols, serums, glosses, powders, and so forth. Certain embodiments can include, for example, (facial and/or body) skin cleansers, scrubs, and/or exfoliants, facial and other masks, including sheet masks, rinse off masks, and/or peel off masks, body coating, wraps, day and/or night treatments, cosmetics, including color cosmetics, foundation, concealer, blush, bronzer, eye shadow, eyeliner, mascara, eyebrow enhancer, lip color, gloss, or balm, and so forth.

Additional features and advantages of exemplary embodiments of the present disclosure will be set forth in the description which follows, and in part will become more fully apparent from the description, or may be learned by the practice of such exemplary embodiments. The features and advantages of such embodiments may also be realized and obtained by means of the instruments and combinations particularly pointed out in the appended claims.

It is also noted that each of the foregoing, following, and/or other features described herein represent a distinct embodiment of the present disclosure. Moreover, combinations of any two or more of such features represent distinct embodiments of the present disclosure. Such embodiments can also be combined in any suitable combination and/or order without departing from the scope of this disclosure. Thus, each of the features described herein can be combinable with any one or more other features described herein in any suitable combination and/or order. Accordingly, the present disclosure is not limited to the specific combinations of exemplary embodiments described in detail herein.

DETAILED DESCRIPTION

Before describing various embodiments of the present disclosure in detail, it is to be understood that this disclosure is not limited to the specific parameters and description of the particularly exemplified systems, methods, and/or products that may vary from one embodiment to the next. Thus, while certain embodiments of the present disclosure will be described in detail, with reference to specific configurations, parameters, features (e.g., components, members, elements, parts, and/or portions), etc., the descriptions are illustrative and are not to be construed as limiting the scope of the present disclosure and/or the claimed invention. In addition, the terminology used herein is for the purpose of describing the embodiments, and is not necessarily intended to limit the scope of the present disclosure and/or the claimed invention.

Unless defined otherwise, all technical and scientific terms used herein have the same meaning as commonly understood by one of ordinary skill in the art to which the present disclosure pertains.

Various aspects of the present disclosure, including systems, methods, and/or products may be illustrated with reference to one or more embodiments or implementations, which are exemplary in nature. As used herein, the terms "embodiment" and implementation" mean "serving as an example, instance, or illustration," and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the description thereof.

As used herein, the term "systems" also contemplates compositions, kits, and so forth. Similarly, the term "method" also contemplates processes, procedures, steps, and so forth. Moreover, the term "products" also contemplates systems, compositions, kits, and so forth.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used in this specification and the appended claims, the singular forms "a," "an" and "the" also contemplate plural referents, unless the context clearly dictates otherwise. Thus, for example, reference to a "molecule" includes one, two, or more molecules. Similarly, reference to a plurality of referents should be interpreted as comprising a single referent and/or a plurality of referents unless the content and/or context clearly dictate otherwise. Thus, reference to "molecules" does not necessarily require a plurality of such molecules. Instead, it will be appreciated that independent of conjugation; one or more molecules are contemplated herein.

It will also be appreciated that where two or more values, or a range of values (e.g., less than, greater than, at least, and/or up to a certain value, and/or between two recited values) is disclosed or recited, any specific value or range of values falling within the disclosed values or range of values is likewise disclosed and contemplated herein. Thus, disclosure of an illustrative measurement (e.g., volume, concentration, etc.) that is less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 units, between 8 units and 2 units, between 6 units and 4 units, and/or any other range of values between 0 and 10 units.

To facilitate understanding, like references (i.e., like naming of components and/or elements) have been used, where possible, to designate like components and/or elements common to the written description and/or figures. Specific language will also be used herein to describe the exemplary embodiments. Nevertheless it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential).

The headings used herein are for organizational purposes only and are not meant to be used to limit the scope of the description or the claims.

Disclosed herein is a skin rejuvenation and defense system. The skin rejuvenation and defense system includes a skin rejuvenation application and a skin defense application that work together synergistically to rejuvenate and defend the skin from environmental insults that can, for instance, accelerate the aging process and deprive the skin of its vitality. Accordingly, in some embodiments, two or more components (e.g., applications, products, compositions, mixtures, etc.) can form a skincare system or kit. Two or more sub-components (e.g., ingredients, elements, parts, etc.) can similarly form each component.

In at least one embodiment, the terms "form," "forming," and the like are open-ended, such that sub-components that (are combined, mixed, or included together so as to) form a component (e.g., system, application, product, composition, mixture, ingredient, element, part, etc.) do not necessarily constitute the entire component. Accordingly, a component can comprise said sub-components, without, necessarily, consisting, either entirely or essentially, of said sub-components, and a system or kit can comprise said components, without, necessarily, consisting, either entirely or essentially, of said components.

As used herein, the terms "mixture," "fluid mixture," "liquid mixture," and the like can comprise any suitable composition and/or combination of the specific components thereof. For instance, a fluid or liquid mixture can comprise a solution, suspension, colloid, emulsion, or other mixture of liquid and non-liquid components.

In an embodiment, the skin rejuvenation application can have anti-aging properties in that it can help restore the vitality and youthful appearance of the skin by plumping the skin. Likewise, the skin rejuvenation application can help fight the effects of toxins and pollutants that can prematurely age the skin. When the skin rejuvenation application is applied to the skin, it can bubble and effervesce; the bubbling action can lift dirt, sebum, dead skin, pollutants, and the like off of the skin. The skin rejuvenation application can also activate the energy systems in the skin, specifically by activating cellular mitochondria in the skin. Likewise, the skin rejuvenation application can penetrate readily into the skin to deliver oxygen to the cells and carry away carbon dioxide.

In an embodiment, the skin rejuvenation application can be specifically formulated to be applied to a skin surface, left on for a selected period of time, and then removed (e.g., by rinsing with water). In an embodiment, the skin rejuvenation application can be formulated to be left on the skin for a period of time ranging from about 30 seconds to about 10 minutes (e.g., about 5-10 minutes).

The skin defense application can be specifically formulated to be applied to the skin surface after removal of the skin rejuvenation application and to be left on the skin (e.g., in the evening before bedtime). In addition, the skin defense application may be applied to the skin again at least one additional time within 6-10 of the initial application (e.g., in the morning).

After the skin has been opened up and made receptive by the skin rejuvenation application, the skin defense application absorbs into the skin to deeply moisturize and revitalize the skin. In addition to moisturizers, emollients, and similar ingredients that improve health and appearance of the skin, the skin defense application includes ingredients that can, for instance, reverse and protect the skin from damage caused by pollutants (e.g., pm2.5 pollutants) and pre- and pro-biotics that the growth and development of beneficial skin flora.

Compositions

In an embodiment, the skin rejuvenation application includes a Snow Algae (*Coenochloris signiensis*) preparation, IBR Snowflake® (*Leucojum aestivum* bulb extract), FiFlow® BB61 (perfluorohexane, perfluorodecalin, and pentafluoropropane), and water.

Snow algae (e.g., *Coenochloris signiensis*) is a type of single-cell, cryophilic algae with the unique ability to actively live at a temperature of approximately 0° C. In contrast, most other plants either reduce their metabolic activities or are simply unable to survive at this temperature. Snow algae grow in areas where there is either an alpine or polar climate in which there is snow all year round (permanent snow). Therefore, these extremophile algae have the ability to thrive in freezing water with very low nutrient levels. *Coenochloris signiensis* is a common type of snow algae.

Snow algae adapt to their environment by modifying their pigmentation: at the beginning of winter, the snow algae enter into a dormant phase, resting in the form of red spores under the snow. In fact, the algae turn red as they produce considerably more carotenoid pigments than chlorophyll ones in order to protect against UV rays. In spring, increased levels of nutrients and light, as well as melted ice, stimulate germination: snow algae cells appear green as they predominantly contain chlorophyll pigments. Chlorophyll absorbs energy from light in order to convert it into chemical energy (carbohydrates) that will fuel the activities of the algae. In addition, the snow algae green cells have a pair of front-mounted flagella that enable individual cells to move around in their environment. Hence, the snow algae can travel towards the surface of the snow where they propagate.

At the end of summer, this growth/reproduction stage alternates with a dormant one. As a result, snow algae green cells transform once again into red spores to survive until the following summer. Pigment concentration change is one of the strategies developed by the snow algae to enable them to adapt to their extreme habitat. Production of other secondary metabolites such as biopolymers (gallerten), antifreeze glycoproteins (AFGPs) stress modifiers and osmotically active amino acids and sugars also help these extremophile algae to survive in their habitat.

Snow algae can be produced commercially in a biofermentation process that mimics conditions in snow algae's natural environment. Firstly, the snow algae grow in a medium supplied with light and air (including $CO_2$) to mimic favorable growth conditions. During this stage, the snow algae take on a green appearance due to the chlorophyll pigments that they contain. Secondly, the level of nutrients is reduced and light is strongly increased. As a consequence, the snow algae start to produce carotenoid pigments in a high concentration to protect against UV rays. Therefore, the snow algae turn red and they are then harvested.

To obtain the snow algae preparation used in the formulations described herein, the cells of the snow algae are homogenized (e.g., at 1200 bar) together with phospholipids to encapsulate and stabilize their oil-soluble and water-soluble components into liposomes. The resulting suspension is carefully sprayed on a powder based on maltodextrin (Snow Algae Powder).

The snow algae preparation used in the formulations described herein offers an anti-aging treatment that is based on a mimicking of calorie restriction. Calorie restriction has been shown to improve both the healthspan and lifespan of individuals and is thus considered to be a promising new anti-aging pathway. Snow Algae Powder mimics the effects of calorie restriction and in this way improves the longevity of skin cells. Consequently, it offers the skin the benefits of a diet without the need to undergo a low-calorie regime.

At the cellular level, Snow Algae Powder protects and activates two key factors of the calorie restriction pathway: the Klotho longevity gene and the AMPK energy sensor that together lead to improved cellular defenses, oxidative stress resistance, cell detoxification and repair. The anti-aging activity of Snow Algae Powder was also confirmed by proteomics technology. The results in the skin are the production of collagen starting again and a rejuvenation of the dermal epidermal junction. Consequently, the skin barrier can be reinforced while the skin appears fresher, detoxified, and moisturized.

In addition, Snow Algae Powder protects and activates longevity factors in skin cells, rejuvenates and protects skin at cellular level, safeguards skin's youthfulness by activating Klotho, strengthens cellular defense mechanisms through calorie restriction mimetic activity, and reinforces, smooths and hydrates the skin.

IBR Snowflake® is an extract of the bulbs of *Leucojum aestivum*. *Leucojum aestivum*, which is commonly called summer snowflake, is a plant species widely cultivated as an ornamental. It is native to most of Europe. *Leucojum aestivum* is a perennial herb up to 60 cm tall with bulbs up to 4 cm across.

*Leucojum aestivum* bulb extract (IBR-Snowflake®) captures and transfers flower bulbs dormancy and rejuvenation to skin. Flower bulbs go dormant through the winter like "beauty sleep" to allow beautiful awaken, rejuvenated blossom in the spring. The IBR anti-aging technology via implementation of DORMINs features slowdown of skin aging as a result of slowing down cell proliferation thereby preserving youth cell capital and improving skin appearance and maturation. Affecting proliferation of various cell types may improve age spot appearance and overall lighten the skin tone.

IBR-Snowflake® has a demonstrated ability to significantly reduce melanin synthesis and slowdown human melanocytes proliferation, serves as strong support to the effect IBR-Snowflake® has on lightening the skin tone. IBR-Snowflake® has also been found to effectively inhibit contraction of muscle cells thereby reducing and preventing wrinkles and fine lines appearance and potentially functioning as a safe substitute to Botox treatment. Additionally, the extract functions as a booster to the natural skin anti-oxidant system and self-defense by increasing SOD (super oxide dismutase) expression, all together enabling *Leucojum aestivum* bulb extract as an ideal active ingredient for whiter, smoother and flawless skin.

FiFlow® BB61 is a cosmetic blend of perfluorocarbons (perfluorohexane, perfluorodecalin, and pentafluoropropane), which have a capacity to carry gases, notably oxygen, nitrogen, and carbon dioxide. Perfluorocarbons are inert materials, and they are not oil soluble or water soluble, hence they create a third phase in emulsions. Perfluorocarbons are stable, heavy liquids and even the most volatile ones are safe to use as they have no flash point. Perfluorocarbons normally contain air, but they can be enriched with other gases such as oxygen. Products with perfluorocarbons need to be packaged in airless packaging. If not, there can be foam formation in the product as the perfluorocarbons evaporate into the surrounding air.

Perfluorocarbons, like FiFlow® BB61, have many potential benefits to the skin. These benefits include fast penetration into the skin, the capacity to carry gases, notably oxygen and carbon dioxide, into and out of the substratal layers of the skin, wound healing, muscular relaxation, dermal filling (i.e., skin plumping), and soft skin feel.

Fiflow® BB61 is an ideal ingredient for anti-wrinkle products as it has an instantaneous dermal filling and muscular relaxation effect. It also has long-term effects due to its capacity to supply Oxygen to the skin. Fiflow® BB61 also improves skin renewal and skin elasticity. Fiflow® BB61 allows the oxygen to be carried gradually into the skin over a long period of time.

In another embodiment, the skin rejuvenation application comprises a blend or mixture of water, a (lightly-cross-linked) acrylate copolymer (commercially available as Carbopol® Aqua SF-1 from Lubrizol, Wickliffe, Ohio), DL-Panthenol 50% liquid (panthenol, water), hydroxyethyl urea, pentylene glycol, decyl glucoside, a surfactant blend comprising water, sodium lauroyl methyl isethionate, cocamidopropyl betaine, sodium methyl oleoyl, taurate, and sodium cocoyl isethionate (commercially available as Iselux® SFS by Innospec Performance Chemicals, Littleton, Colo.).

In an embodiment, the skin rejuvenation application comprises IBR Snowflake® (water, *Leucojum aestivum* bulb extract), Snow Algae preparation (maltodextrin, water, *Coenochloris signiensis* extract, lecithin), propanediol, xanthan gum, aminomethyl propanol (AMP) (commercially available as AMP-ULTRA™ PC 2000 by ANGUS Chemical Company, Buffalo Grove, Ill.) ethoxydiglycol, polysorbate 20, Botanistat PF-64™ (Phenoxyethanol, Caprylyl Glycol, Ethylhexylglycerin, Hexylene Glycol), aromatic mandarin ginger lily extract blend (caprylic/capric triglyceride, *Citrus aurantium dulcis* (orange) fruit extract, *Citrus aurantium dulcis* (orange) peel extract, *Lavandula angustifolia* (Lavender) flower/leaf/stem extract, *Elettaria cardamomum* seed extract, *Gardenia taitensis* flower extract, *Prunus armeniaca* (apricot) fruit extract, *Pyrus malus* (apple) fruit extract, *Hibiscus abelmoschus* seed extract, *Eugenia caryophyllus* (clove) flower extract, *Vanilla planifolia* fruit extract, *Jasminum officinale* (jasmine) flower/leaf extract, *Hedychium spicatum* extract, *Plumeria rubra* flower extract), and Fiflow® BB61 (perfluorohexane, perfluorodecalin, pentafluoropropane).

In another embodiment, the skin rejuvenation application comprises a blend or mixture of water, perfluorohexane*, pentylene glycol, propanediol, acrylates copolymer, maltodextrin, perfluorodecalin*, pentafluoropropane*, ethoxydiglycol, hydroxyethyl urea, polysorbate 20, panthenol, *citrus aurantium dulcis* (orange) fruit extract*, *citrus aurantium dulcis* (orange) peel extract*, *Lavandula angustifolia* (lavender) flower/leaf/stem extract*, *leucojum aestivum* bulb extract, *Coenochloris signiensis* extract, lecithin, *elettaria cardamomum* seed extract*, *eugenia caryophyllus* (clove) flower extract*, *gardenia taitensis* flower extract*, *hedychium spicatum* extract*, *hibiscus abelmoschus* seed extract*, *jasminum officinale* (jasmine) flower/leaf extract*, *plumeria rubra* rower extract*, *prunus armeniaca* (apricot) fruit extract*, *Pyrus malus* (apple) fruit extract*, vanilla planifolia fruit extract*, aminomethyl propanol, sodium lauroyl methyl isethionate, caprylyl glycol, decyl glucoside, xanthan gum, ethylhexylglycerin, hexylene glycol, caprylic/capric triglyceride*, cocamidopropyl betaine, sodium methyl oleoyl taurate, sodium cocoyl isethionate, phenoxyethanol.

Components (e.g., ingredients) having an asterisk (*) thereafter can be provided in or as (components of) Ox3™ (by Modere™, Springville, Utah).

Some of the properties certain ingredients listed above are shown below in Table 1:

TABLE 1

| | |
|---|---|
| perfluorohexane, | |
| perfluorodecalin, | |
| pentafluoropropane | |
| Snow Algae Powder | |
| Leucojum Aestivum Bulb Extract | |
| Water | Solvent and skin conditioning agent |
| Pentylene Glycol | skin conditioning agent, solvent, preservative booster |
| Propanediol | solvent |
| Acrylates Copolymer | thickening agent, skin conditioning agent |
| Hydroxyethyl urea | A humectant that also improves smoothness and provides lubrication |
| Maltodextrin | skin conditioning agent |
| Panthenol | skin conditioning agent—humectant |
| Decyl Glucoside | A mild, non-ionic surfactant with excellent foaming properties. |
| Sodium Lauroyl Methyl Isethionate | surfactant |
| Cocamidopropyl Betaine | An amphoteric surfactant that is a good cleanser & foam booster, viscosity enhancer, excellent conditioning & antistatic agent, moderate emulsifier. |
| Sodium Methyl Oleoyl Taurate | surfactant |
| Sodium Cocoyl Isethionate | surfactant |
| Lecithin | skin conditioning agent, emulsifier |
| Coenochloris Signiensis Extract | |
| Xanthan Gum | viscosity increasing agent |
| Aminomethyl Propanol | pH adjuster |
| Ethoxydiglycol | solvent—in this formula, this ingredient is used to help solubilize the preservatives |
| Polysorbate 20 | solubilizer—used to solubilize the preservatives |
| Phenoxyethanol | Preservative |
| Caprylyl Glycol | skin conditioning agent, preservative booster |
| Ethylhexylglycerin | skin conditioning agent, preservative booster |
| Hexylene Glycol | solvent, preservative booster |

Additional properties, suggested use levels, and typical use levels of certain ingredients listed above are shown below in Table 2:

TABLE 2

| INCI Name | Function in this formulation | Suggested Use Level | Typical Use Levels* |
|---|---|---|---|
| Water | Water is used in the formulation of most types of cosmetic and personal care products. Water is primarily used as a solvent to dissolve many of the ingredients that impart skin benefits, such as conditioning agents and cleansing agents. Water also forms emulsions in which the oil and water components of the product are combined to form creams and lotions. Only Water that is free of toxins, pollutants and microbes is used in the formulation of cosmetics and personal care products. Water used for this purpose is also referred to as distilled water, purified water or aqua. | 0-100% | 0-100% |
| Perfluorohexane Perfluorodecalin Pentafluoropropane | This formulation contains a mixture of fully fluorinated perfluorocarbons (Trade name: Fiflow ® BB61) with an incredible capacity to carry gases, notably oxygen, nitrogen and carbon dioxide. The perfluorocarbons are inert materials and they are neither oil soluble nor water soluble, hence they create a third phase in emulsions. They are stable, heavy liquids and even the most volatile ones are safe to use as they have no flash point. They always contain air but they can be enriched with other gases such as oxygen. This perfluorocarbon mixture creates a visual bubbling effect due to the gas (or air) content. Gas exchange between the perfluorocarbons and the surrounding air occurs when Infusion is expelled from the bottle and rubbed onto the surface of the skin. This gas exchange results in the formation of many tiny, foaming bubbles. | 2-15% | no data |
| Pentylene Glycol | Pentylene Glycol is a 1,2-glycol compound with a 5 carbon chain length. This compound has a hydroxyl group (—OH) on the first and second carbons. Pentylene Glycol has 5 carbons, 1,2-Hexandiol has 6 carbons and Caprylyl Glycol has 8 carbons in the carbon chain. In cosmetics and personal care products, these ingredients may be used in baby products, bath products, eye makeup, cleansing products, skin care products and hair care products. The following functions have been reported for 1,2-hexanediol: solvents. Pentylene Glycol, 1,2-Hexanediol and Caprylyl Glycol are all soluble in water, with water solubility increasing with decreasing carbon chain length. Although Caprylyl Glycol and Pentylene Glycol have been reported to have some antimicrobial activity, these ingredients may also serve to increase the antimicrobial activity of other preservatives. | 1-5% | CIR report: 0.001 to 5%. |
| Propanediol | Solvent used to boost preservative efficacy, improve skin moisturization and formula sensorial characteristics, This is a natural and highly pure colorless glycol, derived from a sustainable and renewable corn sugar fermentation process. | no use level listed | No data. Estimated use 0.0001%-≤99.4%. |
| Acrylates Copolymer | Acrylates copolymer is a rheology modifier designed to suspend, stabilize, thicken and enhance the | 1.2-10% | CIR report: 0.5-25%. |

TABLE 2-continued

| INCI Name | Function in this formulation | Suggested Use Level | Typical Use Levels* |
|---|---|---|---|
| | appearance of surfactant-based personal cleansing products. In this formula it helps to suspend and stabilize the perfluorocarbon phase such that it is uniform throughout the gel. | | |
| Maltodextrin | This ingredient is derived from starch and is used as a base for some plant extracts. Maltodextrin is the saccharide material obtained by hydrolysis of starch. Maltodextrin is an absorbent; binder; emulsion stabilizer; film forming; skin-conditioning agent. | not listed | CIR report: 0.0001 to 4%. |
| Ethoxydiglycol | Ethoxydiglycol is a clear, practically colorless, liquid. Ethoxydiglycol is used as a solvent and/or a viscosity decreasing agent in cosmetics and personal care products. It is a glycol or glycol ether. Glycols are a class of alcohols that contain two hydroxyl groups which are also called a diols. | not listed | CIR report: 0.00004-80% |
| Hydroxyethyl Urea | Hydroxyethyl Urea acts as a humectant in cosmetics and personal care products. Humectants help to bind water and maintain moisturization of the skin. It is an excellent moisturizer that diffuses into the skin to alleviate dryness. This ingredient can absorb 82% of its weight in water and works to increase the elasticity of the skin and improve the overall feel of the formula. | 1-20% | no data |
| Polysorbate 20 | Polysorbate 20 and the other Polysorbate ingredients are a series of general purpose hydrophilic, nonionic surfactants. The Polysorbate ingredients help other ingredients to dissolve in a solvent in which they would not normally dissolve. They also help to form emulsions by reducing the surface tension of the substances to be emulsified. Polysorbates are surfactants that are produced from sorbitol and fatty acids. Polysorbates function to disperse oil in water as opposed to water in oil. Often they are used to solubilize fragrances or essential oils in shampoos, body washes and other surfactant gel products. | not listed | CIR report: ≤19.6% |
| Phenoxyethanol | Phenoxyethanol is an oily, slightly viscous liquid with a faint rose-like odor. Phenoxyethanol prevents or retards microbial growth, and thus protects cosmetics and personal care products from spoilage. It may also be used in fragrances. Phenoxyethanol is usually synthesized for commercial use but it can also be found naturally in products such as green tea. | regulatory maximum 1.0% | CIR report: 0.0002-1% |
| Panthenol | Panthenol is derived from vitamin B5, also know as Pantothenic Acid. Panthenol acts as a lubricant on the skin surface, which gives the skin a soft and smooth appearance. Panthenol and Pantothenic Acid also enhance the appearance and feel of hair, by increasing hair body, suppleness, or sheen, or by improving the texture of hair that has been damaged physically or by chemical treatment. Panthenol and Pantothenic Acid (vitamin B5) have the same biological activity and Panthenol can be converted (by oxidation) to | 0.1-5.0% | CIR report: 0.00005 to 6%. |

TABLE 2-continued

| INCI Name | Function in this formulation | Suggested Use Level | Typical Use Levels* |
|---|---|---|---|
| | vitamin B5 in the skin. Pantothenic Acid is found in all living cells and tissues and is essential for normal metabolism and hormone production. In cosmetics and personal care products, two forms of Panthenol can be found: D-Panthenol occurs as a viscous oil and DL-Panthenol occurs as a creamy white, crystalline powder. | | |
| Aminomethyl Propanol | pH Adjustor | not listed | CIR report: ≤7%, but regulatory maximum limit in U.S. appears to be 1.0% |
| Sodium Lauroyl Methyl Isethionate | An extremely mild, GMO-free, surfactant made from botanical and synthetic sources. Sodium Lauroyl Methyl Isethionate produces a dense, luxurious foam, elegant after-feel, and outstanding rinseability. | not listed | CIR report: 0.23-49.4% |
| Caprylyl Glycol | Caprylyl Glycol is an 8 carbon chain, 1,2-glycol compound. This means that it has a hydroxyl group (—OH) on the first and second carbons. The following functions have been reported for Caprylyl Glycol: Deodorant Agent, Hair Conditioning Agent, Preservative, and Skin-Conditioning Agent—Emollient. Caprylyl Glycol is soluble in water. Although Caprylyl Glycol has been reported to have some antimicrobial activity, it may also serve to increase the antimicrobial activity of other preservatives. | 0.3-1.0% | CIR report: 0.00003-5% |
| Decyl Glucoside | A mild, non-ionic surfactant with excellent foaming properties that washes away sebum and other impurities from the skin without excessive drying. Alkyl glucoside ingredients are formed by reacting a fatty alcohol or mixtures of fatty alcohols (that vary by carbon chain length) with a cyclic form of the sugar, glucose or glucose polymers. Decyl Glucoside is formed by reacting a 10 carbon chain alcohol, decyl alcohol, with a cyclic form of glucose. In cosmetics and personal care products, Decyl Glucoside functions as a surfactant—cleansing agent. Alkyl glucosides include alkyl groups bound to glucose in the D-glycopyranoside form. The glucose portion of the compound may include mono-, di-, tri-, oligo- or polysaccharides. For example, Decyl Glucoside with a degree of polymerization of 1.6 is a mixture of decyl monosaccharide (glucopyranoside) and decyl disaccharide (also called maltopyranoside). | not listed | CIR report: ≤33%, |
| Xanthan Gum | Xanthan Gum is a polysaccharide derived from the fermentation of carbohydrates. Xanthan Gum is derived from glucose or corn syrup. In cosmetics and personal care products, Xanthan Gum may function as a binder, emulsion stabilizer, skin-conditioning agent—miscellaneous, surfactant—emulsifying agent, or viscosity increasing agent—aqueous. | 0.2-1.0% | CIR report: ≤5% |

TABLE 2-continued

| INCI Name | Function in this formulation | Suggested Use Level | Typical Use Levels* |
|---|---|---|---|
| | Xanthan Gum is a very large molecule with an average molecular weight of 1,000,000 or more. Xanthan Gum dissolves readily in water with stirring, resulting in highly viscous solutions at low concentrations. | | |
| Ethylhexylglycerin | Ethylhexylglycerin is alkyl glyceryl ether. This means that the ethylhexyl group is bound to glycerin at one end by an ether linkage. The following functions have been reported for Ethylhexylglycerin: Deodorant agent, skin-conditioning agent—miscellaneous. The alkyl glyceryl ether ingredients, including Ethylhexylglycerin are solids at room temperature and are generally poorly soluble in water. Ethylhexylglycerin may enhance the function of preservatives by affecting the cell walls of bacteria promoting destruction of the bacteria by the preservative. | 0.3-1.0% | CIR report: 0.000001-8% |
| Hexylene Glycol | Hexylene Glycol is a clear, practically colorless, liquid. It is used as a solvent, a viscosity decreasing agent and a preservative booster in cosmetics and personal care products. Glycols, sometimes called glycol ethers, are a class of alcohols that contain two hydroxyl groups which are also called a diols. | not listed | CIR report: 0.0009-6% |
| Caprylic/Capric Triglyceride | Caprylic/Capric Triglyceride is an emollient ester derived from Coconut and Palm Oil fatty acids. It is widely used in cosmetic and personal care products for its skin conditioning and moisturizing properties. | not listed | CIR report: 0.00001-84% |
| Cocamidopropyl Betaine | A coconut-derived surfactant used in shampoos to add mildness and thickness. Cocamidopropyl Betaine is part of a class of chemicals called amidopropyl betaines. These compounds consist of various fatty acids bound to amidopropyl betaine. The fatty acids in Cocamidopropyl Betaine are derived from coconut oil. Functions reported for Cocamidopropyl Betaine include: antistatic agent, hair conditioning agent, skin-conditioning agent—miscellaneous, surfactant—cleansing agent, surfactant—foam booster and viscosity increasing agent—aqueous. | not listed | CIR report: 0.005 to 11%. |
| Sodium Methyl Oleoyl Taurate | A mild, sulfate-free, anionic surfactant, derived from plant-based resources, that is often used in personal cleansing applications such as shampoo and body washes | not listed | CIR survey is underway. Data has not yet been reported |
| Sodium Cocoyl Isethionate | An extremely mild surfactant, derived from coconut oil, that leaves the skin feeling soft and silky and is completely biodegradable | not listed | CIR report: 0.23-49.4% |
| Citrus Aurantium Dulcis (Orange) Fruit Extract | This is an aromatic extract that contributes to the scent of the product and helps to condition the skin. | not listed | no data |
| Citrus Aurantium Dulcis (Orange) Peel Extract | This is an aromatic extract that contributes to the scent of the product and helps to condition the skin. | not listed | no data |
| Lavandula Angustifolia (Lavender) Flower/Leaf/Stem Extract | This is an aromatic extract that contributes to the scent of the product and helps to condition the skin. | not listed | no data |
| *Leucojum Aestivum* Bulb | *Leucojum aestivum* (commonly called summer snowflake) is a | 2% for IBR- | No data. Estimated |

TABLE 2-continued

| INCI Name | Function in this formulation | Suggested Use Level | Typical Use Levels* |
|---|---|---|---|
| Extract | perennial flower bulb species that is widely cultivated as a garden flower. It is native to most of Europe, Turkey, Iran and the Caucasus. This extract helps to slowdown aging, increase natural skin defenses by enhancing SOD production and make the skin look brighter and smoother. | Snowflake @ blend | use 0.00001-2.0% for IBR-Snowflake ® blend |
| *Coenochloris Signiensis* Extract | *Coenochloris Signiensis* is a unique extremophile algae species that has managed to develop survival strategies that enable it to grow on glaciers and in permanent snow. It is a terrestrial species found in the Antarctic and sub Antarctic islands, South Orkney Islands and Iceland. This extract mimics the effects of calorie restriction and in this way improves the longevity of the skin cells. At the cellular level, this extract protects and activates two key factors of the calorie restriction pathway: the Klotho longevity gene and the AMPK energy sensor that together lead to improved cellular defenses, oxidative stress resistance, cell detoxification and repair. The antiaging activity of this extract was also confirmed by proteomics technology. The results in skin are the production of collagen and rejuvenation of the dermal epidermal junction. Consequently, the skin barrier is reinforced and the skin is better moisturized, while the skin appears fresher as age spots are less visible. | 2-3% for Snow Algae Powder blend | No data. Estimated use 0.00001-3% |
| Lecithin | Lecithin is a naturally occurring mixture of the diglycerides of stearic, palmitic and oleic acids, linked to the choline ester of phosphoric acid whose form varies from a waxy mass to a thick, pourable liquid. Hydrogenated Lecithin is the product of controlled hydrogenation (addition of hydrogen) of Lecithin. Lecithin enhances the appearance of dry or damaged skin by reducing flaking and restoring suppleness. This ingredient also helps to form emulsions by reducing the surface tension of the substances to be emulsified. Lecithin can be found in all living organisms and is a predominant component of nervous tissue. It can be obtained from soybean, corn, and egg yolks. Although Lecithin includes diglycerides of stearic, palmitic and oleic acids, the exact fatty acid composition of Lecithin varies depending on the source from which it was obtained. | not listed | CIR report: 0.00000008-50% |
| Elettaria Cardamomum Seed Extract | This is an aromatic extract that contributes to the scent of the product and helps to condition the skin. | not listed | no data |
| Eugenia Caryophyllus (Clove) Flower Extract | This is an aromatic extract that contributes to the scent of the product and helps to condition the skin. | not listed | no data |
| Gardenia Taitensis Flower Extract | This is an aromatic extract that contributes to the scent of the product and helps to condition the skin. | not listed | no data |
| Hedychium Spicatum Extract | This is an aromatic extract that contributes to the scent of the product and helps to condition the skin. | not listed | no data |

TABLE 2-continued

| INCI Name | Function in this formulation | Suggested Use Level | Typical Use Levels* |
|---|---|---|---|
| Hibiscus Abelmoschus Seed Extract | This is an aromatic extract that contributes to the scent of the product and helps to condition the skin. | not listed | no data |
| Jasminum Officinale (Jasmine) Flower/Leaf Extract | This is an aromatic extract that contributes to the scent of the product and helps to condition the skin. | not listed | no data |
| Plumeria Rubra Flower Extract | This is an aromatic extract that contributes to the scent of the product and helps to condition the skin. | not listed | no data |
| Prunus Armeniaca (Apricot) Fruit Extract | This is an aromatic extract that contributes to the scent of the product and helps to condition the skin. | not listed | no data |
| Pyrus Malus (Apple) Fruit Extract | This is an aromatic extract that contributes to the scent of the product and helps to condition the skin. | not listed | no data |
| Vanilla Planifolia Fruit Extract | This is an aromatic extract that contributes to the scent of the product and helps to condition the skin. | not listed | no data |

*Cosmetic Use: The Cosmetic Ingredient Review (CIR) Expert Panel assesses the safety of cosmetic ingredients based on the expected use of these ingredients in cosmetics. The Panel reviews data received from the U.S. Food and Drug Administration (FDA) and the cosmetics industry to determine the expected cosmetic use. The FDA collects data from manufacturers on the use of individual ingredients in cosmetics, by cosmetic product category, through the FDA Voluntary Cosmetic Registration Program (VCRP). Data from the cosmetic industry are submitted in response to a survey of the maximum reported use concentrations, by category, conducted by the Personal Care Products Council.

Some embodiments include a skin defense application, alone or in combination with a skin rejuvenation application. In an embodiment, the skin defense application includes (a blend or mixture of) Apolluskin® (*Taraxacum officinale* (dandelion) extract), Ecoskin® (alpha-glucan oligosaccharide, *Polymnia sonchifolia* root juice, maltodextrin, *Lactobacillus*), an emulsifier, a moisturizer, and/or water. In an embodiment, the emulsifier and the moisturizer of the skin defense application comprises (i) butylene glycol, (ii) shea butter, (iii) hydroxyethyl urea, (iv) propanediol, (v) a gelling agent (e.g., with emulsifying properties), comprising sodium acrylates copolymer and lecithin (commercially available as Lecigel™ from Lucas Meyer Cosmetics, France), and (vi) an emulsifying agent, comprising polyglyceryl-6 distearate, jojoba esters, polyglyceryl-3 beeswax, and cetyl alcohol (commercially available as Emulium® Meliffera (Emulsifier 75C) from Gattefossé SAS, France).

Apolluskin® (*Taraxacum officinale* (dandelion) extract) is a natural anti-pollution shield. Obtained from dandelion (*Taraxacum officinale*) and rich in fructans, Apolluskin® protects the skin from environmental contamination effects. By limiting inflammation and proteins oxidation that are induced by pollution, Apolluskin® improves the radiance and the skin grain, thus allowing the polluted skin to recover radiant skin characteristics.

Apolluskin® is an antipollution shield active, which protects the skin from repeated environmental aggressions that lead to premature aging. Rich in fructans derived from the Dandelion, Apolluskin® reduces the accumulation of oxidized proteins from environmental pollutants, trapping them, and once removed leaving an improved radiance, complexion, and skin grain. In-vivo tests illustrated that benzo[a]pyrene, a pollutant commonly found in cigarette smoke was actually similar to that of inner-city pollution, and that living in a polluted environment was equivalent to smoking ten cigarettes a day making smokers the perfect volunteer for study. Apolluskin® applied to a group of smoking volunteers revealed that after use of the active smokers had decreased the oxidized proteins on their skin to a point comparable to that of the non-smoking group. The removal of these environmental stressors augmented the complexion with an increased radiance.

Ecoskin® (a mixture of Alpha-glucan oligosaccharide, *Polymnia sonchifolia* root juice, Maltodextrin, and *Lactobacillus* sp. bacteria) is a pre/probiotic complex, spray dried on maltodextrin, made of: α-glucooligosaccharides (GOS), obtained by enzymatic synthesis, from vegetal substrates (corn maltose, beetroot saccharose), 100% pure plant juice, rich in ß-fructooligosaccharides (FOS), obtained by cold pressing, of jicama or yacon tubers (*Polymnia sonchifolia*), *Lactobacillus* probiotic bacteria (*L. casei, L. acidophilus*), inactivated by tyndallization and freeze-dried.

Ecoskin® is a second generation of Bioecolia that provides both prebiotic and probiotic properties. The prebiotic portion is from the alpha-glucan oligosaccharide (Bioecolia) and the beta-fructo oligosaccharide from the cold-pressed extract of jicama; these prebiotics stimulate the skin's ecoflora. The probiotics in Ecoskin® are the inactivated *Lactobacillus* bacteria which stimulate the ß-defensins that are involved in the skin's defense system. The strains of *Lactobacillus* probiotic bacteria (*Lactobacillus casei* and *Lactobacillus acidophilus*) that are used in Ecoskin® are previously freeze-dried and tyndallized, meaning their reproductive system is inactivated by heat which prevents them from developing in the cosmetic formulations containing them. The additional benefits for Ecoskin® include an improvement of skin radiance by a restructuring and smoothing effect.

Hydroxyethyl urea (Hydrovance®) is a single moisturizing agent that delivers moisturization efficacy comparable to the leading benchmark (i.e., glycerin) while offering non-tacky, non-greasy aesthetic in skin care products. This moisturizing agent, delivered in aqueous solution, can provide cost effectiveness as compared to high end moisturizing agents or by reducing glycerin, silicones and aesthetic enhancing agents. Moisture enhancement has been observed with glycerin and other moisturizing agents. Due to excellent moisturizing effects, sensorial experience and safety to skin and eye, Hydrovance® moisturizing agent is especially useful as a moisturizing agent for skin.

Lecigel™ (sodium acrylates copolymer and lecithin) is a gelling agent with emulsifying properties. It allows the increase in the viscosity and the stability of formulas. Suitable for both cold and hot processes, it also helps to adjust the viscosity at the end of the formulation process. Easy-to-use, it is compatible with most emulsifiers and is stable over a wide range of pH. Especially adapted for the formulation of gel-creams, it provides the typical "phospholipid touch" with a cool, soft and non-greasy skin feel.

Emulium® Meliffera is an emulsifier and texture ingredient (emulsifying agent) comprising (a blend or mixture of) polyglyceryl-6 distearate, jojoba esters, polyglyceryl-3 beeswax and cetyl alcohol. Emulium® Meliffera is formulated to adapt to humidity conditions to provide a light and luxurious feel on the skin.

In an embodiment, the skin defense application includes about 1-5 weight % (wt %, w/w) of the Apolluskin®, about 1-5 wt % of the Ecoskin®, about 3-10 wt % of the butylene glycol, about 0.1-3 wt % of the shea butter, about 0.1-3 wt % of the hydroxyethyl urea, about 0.1-3 wt % of the propanediol, about 0.1-3 wt % of the Lecigel™ (sodium acrylates copolymer and lecithin), about 1-5 wt % of the Emulium® Meliffera, and about 60-80 wt % water.

In another embodiment, the skin defense application comprises a blend or mixture of water, Dissolvine® GL-47-S (Tetrasodium Glutamate Diacetate), Carbopol® Utrez 21 (Acrylates/C10-30 Alkyl Acrylate Crosspolymer), Butylene Glycol, Emulium® mellifera (Emulsifier 75C) (Polyglyceryl-6 Distearate, Jojoba Esters, Polyglyceryl-3 Beeswax, Cetyl Alcohol), Fancol Karite Butter (*Butyrospermum Parkii* (Shea) Butter), Botanisil™ DM-85 (Dimethicone), Symocide® PS (Phenoxyethanol, Decylene Glycol, 1,2-Hexanediol), Zemea® (Propanediol), Apolluskin® (*Taraxacum officinale* (Dandelion) Root Extract), Sym-Diol® 68 (1,2-Hexanediol, Caprylyl Glycol), Nalidone® (Sodium PCA), Vitamin E Blend, Ecoskin® (Alpha-Glucan Oligosaccharide), Floraesters K-20W® (Hydrolyzed Jojoba Esters, water), Allantoin, Hydrovance® (Hydroxyethyl Urea), Aromatic Ginger Yuzu Extract Blend, Lecigel™ (Sodium Acrylates Copolymer and Lecithin), and Citric Acid 50% Solution and Sodium Hydroxide 50% Solution to a pH of about 5.75-6.25.

In another embodiment, the skin defense application comprises a blend or mixture of water, butylene glycol, alpha-glucan oligosaccharide, polyglyceryl-6 distearate, dimethicone, sodium PCA, propanediol, *Butyrospermum parkii* (shea) butter, sodium acrylates copolymer, *Polymnia sonchifolia* root juice, jojoba esters, lecithin, hydrolyzed jojoba esters, polyglyceryl-3 beeswax, *Taraxacum officinale* (dandelion) extract, tocopheryl acetate, *Lactobacillus* sp., *Citrus aurantium dulcis* (orange) peel extract, *Zingiber officinale* (ginger) root extract, *Prunus armeniaca* (apricot) fruit extract, *Plumeria rubra* flower extract, *Lavandula angustifolia* (lavender) flower/leaf/stem extract, *Hedychium spicatum* extract, *Gardenia taitensis* flower extract, *Elettaria cardamomum* seed extract, *Cocos nucifera* (coconut) fruit extract, *Citrus tangerina* (tangerine) peel extract, *Citrus junos* peel extract, *Citrus grandis* (grapefruit) fruit extract, *Calendula officinalis* flower extract, hydroxyethyl urea, 1,2-hexanediol, maltodextrin, acrylates/C10-30 alkyl acrylate crosspolymer, caprylyl glycol, decylene glycol, allantoin, cetyl alcohol, tetrasodium glutamate diacetate, caprylic/capric triglyceride, ethylhexylglycerin, phenoxyethanol.

An embodiment (or specific formulation) for the Skin Defense Application can comprise, for example, on a weight/weight basis (w/w): 80.81% water, 5.00% Butylene Glycol, 2.10% Alpha-glucan oligosaccharide, 1.69% Polyglyceryl-6 Distearate, 1.50% Dimethicone, 1.00% Sodium PCA, 1.00% Propanediol, 1.00% *Butyrospermum parkii* (Shea) Butter, 0.79% Phenoxyethanol, 0.75% Sodium Acrylates Copolymer, 0.57% *Polymnia sonchifolia* Root Juice, 0.50% Hydroxyethyl Urea, 0.44% Jojoba Esters, 0.34% 1,2-Hexanediol, 0.30% Maltodextrin, 0.30% Acrylates/C10-30 Alkyl Acrylate Crosspolymer, 0.25% Lecithin, 0.25% Caprylyl Glycol, 0.24% Decylene Glycol, 0.20% Hydrolyzed Jojoba Esters, 0.19% Allantoin, 0.19% Polyglyceryl-3 Beeswax, 0.19% Cetyl Alcohol, 0.13% *Taraxacum officinale* (Dandelion) Extract, 0.10% Tocopheryl Acetate, 0.05% Tetrasodium Glutamate Diacetate, 0.03% *Lactobacillus*, 0.01% *Citrus aurantium dulcis* (Orange) Peel Extract, 0.01% Caprylic/Capric Triglyceride, 0.01% *Zingiber officinale* (Ginger) Root Extract, 0.01% *Prunus armeniaca* (Apricot) Fruit Extract, 0.01% *Plumeria rubra* Flower Extract, 0.01% *Lavandula angustifolia* (Lavender) Flower/Leaf/Stem Extract, 0.01% *Hedychium spicatum* Extract, 0.01% *Gardenia taitensis* Flower Extract, 0.01% *Elettaria cardamomum* Seed Extract, 0.01% *Cocos Nucifera* (Coconut) Fruit Extract, 0.01% *Citrus Tangerina* (Tangerine) Peel Extract, 0.01% *Citrus Junos* Peel Extract, 0.01% *Citrus Grandis* (Grapefruit) Fruit Extract, 0.01% *Calendula Officinalis* Flower Extract, and/or 0.01% Ethylhexylglycerin. Certain embodiments can also comprise quantum satis (qs) Citric Acid and/or Sodium Hydroxide (as needed).

Some embodiments (or formulation) for the Skin Defense Application can comprise, for example, on a weight/weight basis (w/w), about: 50-90% water, 1-10% Butylene Glycol, 0.05-5% Alpha-glucan oligosaccharide, 0.05-5% Polyglyceryl-6 Distearate, 0.05-5% Dimethicone, 0.01-3% Sodium PCA, 0.01-3% Propanediol, 0.01-3% *Butyrospermum Parkii* (Shea) Butter, 0.01-2.5% Phenoxyethanol, 0.01-2.5% Sodium Acrylates Copolymer, 0.01-2.5% *Polymnia sonchifolia* Root Juice, 0.01-2.5% Hydroxyethyl Urea, 0.01-2.5% Jojoba Esters, 0.01-2.5% 1,2-Hexanediol, 0.01-2.5% Maltodextrin, 0.01-2.5% Acrylates/C10-30 Alkyl Acrylate Crosspolymer, 0.01-2.5% Lecithin, 0.01-2.5% Caprylyl Glycol, 0.01-2.5% Decylene Glycol, 0.01-2.5% Hydrolyzed Jojoba Esters, 0.01-2.5% Allantoin, 0.01-2.5% Polyglyceryl-3 Beeswax, 0.01-2.5% Cetyl Alcohol, 0.01-2.5% *Taraxacum officinale* (Dandelion) Extract, 0.01-2.5% Tocopheryl Acetate, 0.001-2.5% Tetrasodium Glutamate Diacetate, 0.001-2.5% *Lactobacillus*, 0.001-2.5% *Citrus aurantium dulcis* (Orange) Peel Extract, 0.001-2.5% Caprylic/Capric Triglyceride, 0.001-2.5% *Zingiber officinale* (Ginger) Root Extract, 0.001-2.5% *Prunus armeniaca* (Apricot) Fruit Extract, 0.001-2.5% *Plumeria Rubra* Flower Extract, 0.001-2.5% *Lavandula angustifolia* (Lavender) Flower/Leaf/Stem Extract, 0.001-2.5% *Hedychium spicatum* Extract, 0.001-2.5% *Gardenia taitensis* Flower Extract, 0.001-2.5% *Elettaria cardamomum* Seed Extract, 0.001-2.5% *Cocos Nucifera* (Coconut) Fruit Extract, 0.001-2.5% *Citrus Tangerina* (Tangerine) Peel Extract, 0.001-2.5% *Citrus Junos* Peel Extract, 0.001-2.5% *Citrus Grandis* (Grapefruit) Fruit Extract, 0.001-2.5% *Calendula Officinalis* Flower Extract, and/or 0.001-2.5% Ethylhexylglycerin. Certain embodiments can also comprise quantum satis (qs) Citric Acid and/or Sodium Hydroxide (as needed).

Additional properties, suggested use levels, and typical use levels of certain ingredients described herein (for the Skin Defense Application) are shown below in Table 3:

TABLE 3

| INCI Name | Function in this formulation | Suggested Use Level | Typical Use Levels * |
|---|---|---|---|
| Water | Water is used in the formulation of most types of cosmetic and personal care products. Water is primarily used as a solvent to dissolve many of the ingredients that impart skin benefits, such as conditioning agents and cleansing agents. Water also forms emulsions in which the oil and water components of the product are combined to form creams and lotions. Only Water that is free of toxins, pollutants and microbes is used in the formulation of cosmetics and personal care products. Water used for this purpose is also referred to as distilled water, purified water or aqua. | 0-100% | 0-100% |
| Butylene Glycol | Butylene Glycol is a clear, practically colorless, liquid. Butylene Glycol is used as a solvent and viscosity decreasing agent in cosmetics and personal care products. Butylene Glycol, or 1,3-Butanediol, dissolves most essential oils and synthetic flavoring substances. Butylene Glycol is a glycol or glycol ether. Glycols are a class of alcohols that contain two hydroxyl groups which are also called a diols. | not listed | CIR report: 0.00007-89% |
| Alpha-glucan oligosaccharide | Alpha-glucan oligosaccharide is a glucose polymer prepared by the action of a glucosyl transferase enzyme on sucrose. In personal care products it is used as a skin-conditioning agent. | approximately 0.1-3% | no data |
| Polyglyceryl-6 Distearate | Polyglyceryl-6 Distearate is used as an emollient and emulsifier in personal care formulations. It is a diester of stearic acid and polyglycerin-6 (a polymer made up of 6 units of glycerin). | approximately 0.5-5% | no data |
| Dimethicone | Dimethicone is a silicone based polymer. The following functions have been reported for Dimethicone: antifoaming agent, skin-conditioning agent, skin protectant. Silicon is ubiquitous in the earth and silicon dioxide is common sand. Silicon, like carbon, can form polymers. Dimethicone is a fluid mixture of siloxane polymers sometimes referred to as polydimethylsiloxane (PDMS). It is optically clear, and is generally considered to be inert, non-toxic and non-flammable. Dimethicone is the most widely used silicone polymer, and is particularly known for its unusual rheological (or flow) properties. | not listed | CIR report: 0.001-80% across all product types but was 0.5-10% for moisturizers |
| Sodium PCA | In cosmetics and personal care products, PCA (pyrrolidonecarboxylic acid) is used mostly in the formulation of conditioners and moisturizers. PCA and Sodium PCA increase the water content of the top layers of the skin by drawing moisture from the surrounding air. They also enhance the appearance and feel of hair, by increasing hair body, suppleness, or sheen, or by improving the texture of hair that | 0.1-3% | CIR report: ≤3.0% |

TABLE 3-continued

| INCI Name | Function in this formulation | Suggested Use Level | Typical Use Levels * |
|---|---|---|---|
| | has been damaged physically or by chemical treatment. PCA, also known pyroglutamic acid or pidolic acid, occurs naturally in mammalian tissues, including the skin. It can be prepared from glutamic acid, an amino acid found in vegetables, fruits, grasses and molasses. | | |
| Propanediol | Solvent used to boost preservative efficacy, improve skin moisturization and formula sensorial characteristics. This is a natural and highly pure colorless glycol, derived from a sustainable and renewable corn sugar fermentation process. | not listed | No data. Estimated use 0.0001%-≤99.4%. |
| Butyrospermum Parkii (Shea) Butter | Butyrospermum Parkii (Shea) Butter is derived from the shea tree, Butyrospermum parkii, also called Vitellaria paradoxa. The following functions have been reported for shea butter: skin conditioning agent—miscellaneous, skin conditioning agent—occlusive, viscosity increasing agent—nonaqueous. The shea tree is native to Central Africa, where it is used as a source of vegetable oil. The oil from the fruit of the shea tree contains about 45-50% oleic acid, 30-41% stearic acid, 5-9% plamitic acid and 4-5% linoleic acid. | not listed | CIR report: ≤60.0% |
| Phenoxyethanol | Phenoxyethanol is an oily, slightly viscous liquid with a faint rose-like odor. Phenoxyethanol prevents or retards microbial growth, and thus protects cosmetics and personal care products from spoilage. It may also be used in fragrances. Phenoxyethanol is usually synthesized for commercial use but it can also be found naturally in products such as green tea. | regulatory maximum 1.0% | CIR report: 0.0002-1% |
| Sodium Acrylates Copolymer | Binder; Viscosity Increasing Agent | approximately 0.1-2% | Estimate from CR report: 0.5-2.0% |
| Polymnia Sonchifolia Root Juice | Skin-Conditioning Agent. Polymnia Sonchifolia Root Juice is sold commercially as a product called Ecoskin ®. | approximately 0.01-3% | no data |
| Hydroxyethyl Urea | Hydroxyethyl Urea acts as a humectant in cosmetics and personal care products. Humectants help to bind water and maintain moisturization of the skin. It is an excellent moisturizer that diffuses into the skin to alleviate dryness. This ingredient can absorb 82% of its weight in water and works to increase the elasticity of the skin and improve the overall feel of the formula. | 1-20% | no data |
| Jojoba Esters | Simmondsia Chinensis (Jojoba) Seed Oil and Simmondsia Chinensis (Jojoba) Seed Wax, also called Jojoba Oil and Jojoba Wax, are natural ingredients derived from the seeds of the desert shrub, Simmondsia chinensis. Jojoba Esters is one of several ingredients made from | approximately 0.1-4% | CIR report: 0.000005-44% |

TABLE 3-continued

| INCI Name | Function in this formulation | Suggested Use Level | Typical Use Levels * |
|---|---|---|---|
| | jojoba oil. The following functions have been reported for Jojoba Esters: Skin-conditioning agents—emollient. Simmondsia Chinensis (Jojoba) Seed Oil is obtained by pressing the seed kernels of an evergreen shrub native to the Sonoran and Mojave deserts of Arizona, California and Mexico. This oil is different from other common plant oils in that it is composed almost completely (97%) of wax esters of monounsaturated, straight-chain acids and alcohols with high molecular weights (carbon chain lengths from 36 to 46). This makes Jojoba Oil and its derivative Jojoba Esters more similar to sebum and whale oil than to traditional vegetable oils. | | |
| 1,2-Hexanediol | 1,2-Hexanediol is a 6 carbon 1,2-glycol compound, which means that it has a hydroxyl group (—OH) on the first and second carbons. It is soluble in water and has been reported to function as a solvent in cosmetic formulations. Although it has been reported to have some antimicrobial activity, 1,2-hexanediol may also serve to increase the antimicrobial activity of other preservatives. | approximately 0.25-1.5% | CIR report: 0.00005-10% |
| Maltodextrin | This ingredient is derived from starch and is used as a base for some plant extracts. Maltodextrin is the saccharide material obtained by hydrolysis of starch. Maltodextrin is an absorbant; binder; emulsion stabilizer; film forming; skin-conditioning agent. | not listed | CIR report: 0.0001 to 4%. |
| Acrylates/C10-30 Alkyl Acrylate Crosspolymer | An emulsion stabilizing, film forming, and viscosity controlling agent that also supports skin hydration balance. Acrylates/C10-30 Alkyl Acrylate Crosspolymer is a copolymer of C10-30 alkyl acrylate and one or more monomers of acrylic acid, methacrylic acid or one of their simple esters crosslinked with an allyl ether of sucrose or an allyl ether of pentaerythritol. In cosmetics and personal care products, Acrylates Crosspolymers are used in a wide variety of product types. The following functions have been reported for Acrylates/C10-30 Alkyl Acrylate Crosspolymer: Emulsion stabilizers, viscosity increasing agents- aqueous, viscosity increasing agents - nonaqueous. | 0.1-6% | CIR report: ≤5% |
| Lecithin | Lecithin is a naturally occurring mixture of the diglycerides of stearic, palmitic and oleic acids, linked to the choline ester of phosphoric acid whose form varies from a waxy mass to a thick, pourable liquid. Hydrogenated Lecithin is the product of controlled hydrogenation (addition of hydrogen) of Lecithin. Lecithin enhances the appearance of dry or damaged skin by reducing flaking | not listed | CIR report: 0.00000008-50% |

TABLE 3-continued

| INCI Name | Function in this formulation | Suggested Use Level | Typical Use Levels * |
|---|---|---|---|
| | and restoring suppleness. This ingredient also helps to form emulsions by reducing the surface tension of the substances to be emulsified. Lecithin can be found in all living organisms and is a predominant component of nervous tissue. It can be obtained from soybean, corn, and egg yolks. Although Lecithin includes diglycerides of stearic, palmitic and oleic acids, the exact fatty acid composition of Lecithin varies depending on the source from which it was obtained. | | |
| Caprylyl Glycol | Caprylyl Glycol is an 8 carbon chain, 1,2-glycol compound. This means that it has a hydroxyl group (—OH) on the first and second carbons. The following functions have been reported for Caprylyl Glycol: Deodorant Agent, Hair Conditioning Agent, Preservative, Skin-Conditioning Agent—Emollient. Caprylyl Glycol is soluble in water. Although Caprylyl Glycol has been reported to have some antimicrobial activity, it may also serve to increase the antimicrobial activity of other preservatives. | 0.3-1.0% | CIR report: 0.00003-5% |
| Decylene Glycol | Decylene Glycol is an antimicrobial agent and skin conditioner that adds slip or lubricity to a formula. It is used as a moisturizer and although it has been reported to have some antimicrobial activity, decylene glycol may also serve to increase the antimicrobial activity of other preservatives. | ≤1.4% | No data. Estimated use 0.00005-10% |
| Hydrolyzed Jojoba Esters | Simmondsia Chinensis (Jojoba) Seed Oil and Simmondsia Chinensis (Jojoba) Seed Wax, also called Jojoba Oil and Jojoba Wax, are natural ingredients derived from the seeds of the desert shrub, Simmondsia chinensis. Jojoba Esters is one of several ingredients made from jojoba oil. The following functions have been reported for Jojoba Esters: Skin-conditioning agents—emollient. Simmondsia Chinensis (Jojoba) Seed Oil is obtained by pressing the seed kernels of an evergreen shrub native to the Sonoran and Mojave deserts of Arizona, California and Mexico. This oil is different from other common plant oils in that it is composed almost completely (97%) of wax esters of monounsaturated, straight-chain acids and alcohols with high molecular weights (carbon chain lengths from 36 to 46). This makes Jojoba Oil and its derivative Jojoba Esters more similar to sebum and whale oil than to traditional vegetable oils. | approximately 0.01-2% | CIR report: 0.0002-2% |
| Allantoin | Allantoin is a white odorless powder. Allantoin is used in the formulation of bath products, eye makeup, hair care products, oral hygiene products and skin care products. Allantoin functions as | 0.1-0.5% | CIR report: 0.0001-2% |

TABLE 3-continued

| INCI Name | Function in this formulation | Suggested Use Level | Typical Use Levels * |
|---|---|---|---|
| | a skin-conditioning agent—miscellaneous. Allantoin also functions as a skin protectant (An ingredient that temporarily protects injured or exposed skin from harmful or annoying stimuli, and that may provide relief to such skin. In the United States, skin protectants are regulated as Over-The-Counter (OTC) drug ingredients). With the exception of humans and higher apes, Allantoin is found in the urine of mammals. It is the primary form in which nitrogen-containing waste is excreted in the urine of these animals. Allantoin is also found in many plants, such as comfrey, horse chestnut and bearberry. Although Allantoin can be isolated from these plants, most Allantoin used in cosmetics and personal care products is made from urea and glyoxylic acid. | | |
| Polyglyceryl-3 Beeswax | An emulsifier prepared from beeswax fatty acids and polyglyceryl-3 (a three unit polymer of glycerin). | approximately 0.05-4% | no data |
| Cetyl Alcohol | Cetyl Alcohol is a fatty alcohol and is widely used in cosmetics and personal care products, especially in skin lotions and creams. It is commonly used as an emollient and viscosity and improve the uniformity and stability of the product. Cetyl Alcohol is a white, waxy solid. | not listed<br><br>to increase | CIR report: 0.000002-15% |
| Taraxacum Officinale (Dandelion) Extract | Skin-Conditioning Agent | approximately 0.01-3% | no data |
| Tocopheryl Acetate | Tocopherol, or vitamin E, a fat-soluble vitamin is a naturally occurring antioxidant which can be isolated from vegetable oil. When isolated, Tocopherol is a viscous oil that varies in color from yellow to brownish red. Rather than Tocopherol itself, esters of Tocopherol are often used in cosmetic and personal care products. These esters include, Tocopheryl Acetate, the acetic acid ester of Tocopherol. In cosmetics and personal care products, Tocopherol Acetate is used in the formulation of lipstick, eye shadow, blushers, face powders and foundations, moisturizers, skin care products, bath soaps and detergents, hair conditioners, and many other products. Tocopheryl Acetate functions as an antioxidant and a skin-conditioning agent. Tocopherol, a fat-soluble vitamin, is found in vegetable fats and oils, dairy products, meat, eggs, cereals, nuts, and leafy green and yellow vegetables. It is usually present in these foods as mixtures of different forms: alpha-, beta-, gamma-, and delta-Tocopherol. The alpha form has the same biological activity as vitamin E. | not listed | CIR report: ≤36% |

TABLE 3-continued

| INCI Name | Function in this formulation | Suggested Use Level | Typical Use Levels * |
|---|---|---|---|
| | Tocopherols can be produced from vegetable oils or can be synthesized. Tocopherol Acetate, made by the esterification of Tocopherol with acetic acid, is frequently the source of vitamin E in dietary supplements. | | |
| Tetrasodium Glutamate Diacetate | Chelating Agent | 0.05-0.5% | no data |
| Lactobacillus | A probiotic bacterial preparation made from Lactobacillus casei and Lactobacillus acidophilus that are previously freeze-dried and tyndallized, meaning their reproductive system is inactivated by heat which prevents them from developing in the cosmetic formulations containing them. | approximately 0.001-3% | no data |
| Citrus Aurantium Dulcis (Orange) Peel Extract | A number of ingredients made from sweet oranges, including Citrus Aurantium Dulcis (Orange) Peel Extract, maybe used in cosmetics and personal care products. It may be used as a Skin-conditioning agent— miscellaneous or Fragrance ingredient. Orange trees probably originated in Southeast Asia. Oranges are now widely cultivated in the tropics and subtropics. Sweet oranges, also know by the Latin name Citrus sinensis, include navel oranges, Valencia oranges and blood oranges. | not listed | no data |
| Caprylic/Capric Triglyceride | Caprylic/Capric Triglyceride is an emollient ester derived from Coconut and Palm Oil fatty acids. It is widely used in cosmetic and personal care products for its skin conditioning and moisturizing properties. | not listed | CIR report: 0.00001-84% |
| Zingiber Officinale (Ginger) Root Extract | This is an aromatic extract that contributes to the scent of the product and helps to condition the skin. | not listed | no data |
| Prunus Armeniaca (Apricot) Fruit Extract | This is an aromatic extract that contributes to the scent of the product and helps to condition the skin. | not listed | no data |
| Plumeria Rubra Flower Extract | This is an aromatic extract that contributes to the scent of the product and helps to condition the skin. | not listed | no data |
| Lavandula Angustifolia (Lavender) Flower/Leaf/Stem Extract | This is an aromatic extract that contributes to the scent of the product and helps to condition the skin. | not listed | no data |
| Hedychium Spicatum Extract | This is an aromatic extract that contributes to the scent of the product and helps to condition the skin. | not listed | no data |
| Gardenia Taitensis Flower Extract | This is an aromatic extract that contributes to the scent of the product and helps to condition the skin. | not listed | no data |
| Elettaria Cardamomum Seed Extract | This is an aromatic extract that contributes to the scent of the product and helps to condition the skin. | not listed | no data |
| Cocos Nucifera (Coconut) Fruit Extract | This is an aromatic extract that contributes to the scent of the product and helps to condition the skin. | not listed | no data |

TABLE 3-continued

| INCI Name | Function in this formulation | Suggested Use Level | Typical Use Levels * |
|---|---|---|---|
| Citrus Tangerina (Tangerine) Peel Extract | This is an aromatic extract that contributes to the scent of the product and helps to condition the skin. | not listed | no data |
| Citrus Junos Peel Extract | This is an aromatic extract that contributes to the scent of the product and helps to condition the skin. | not listed | no data |
| Citrus Grandis (Grapefruit) Fruit Extract | This is an aromatic extract that contributes to the scent of the product and helps to condition the skin. | not listed | no data |
| Calendula Officinalis Flower Extract | Calendula officinalis is a plant known as pot marigold. It should not be confused with other types of plants more commonly known as marigold, such as those in the genus Tagetes. In cosmetics and personal care products, Calendula Officinalis Flower Extract functions as a skin conditioning agent—miscellaneous. Calendula Officinalis Flower Extract may also function as a fragrance ingredient. Calendula officinalis has been used orally and on the skin in traditional herbal medicine, often because of its reported anti-inflammatory activity. Important components of Calendula officinalis include triterpene saponins, flavonoids, and carotenoids, which give the flower the orange and yellow colors. | not listed | CIR report: 0.0001-6% |
| Ethylhexylglycerin | Ethylhexylglycerin is an alkyl glyceryl ether. This means that the ethylhexyl group is bound to glycerin at one end by an ether linkage. The following functions have been reported for Ethylhexylglycerin: Deodorant agent, skin-conditioning agent—miscellaneous. The alkyl glyceryl ether ingredients, including Ethylhexylglycerin are solids at room temperature and are generally poorly soluble in water. Ethylhexylglycerin may enhance the function of preservatives by affecting the cell walls of bacteria promoting destruction of the bacteria by the preservative. | 0.3-1.0% | CIR report: 0.000001-8% |
| Citric Acid | Citric Acid is an organic acid that is widely distributed in plants and animals. Citric Acid and its Diammonium, Potassium and Sodium salts help preserve cosmetics and personal care products by chelating (complexing) metals. Citric Acid and its salts are also added to cosmetics to help adjust the acid/base balance. Citric Acid is a weak organic acid found in citrus fruits, for example, lemon juice contains about 5-8% citric acid. It is also frequently added to soft drinks. Citric Acid is a central compound in the citric acid cycle, a metabolic pathway in essentially all organisms that produces the energy used by cells. | not listed | CIR report: 0.0000005-39% |

TABLE 3-continued

| INCI Name | Function in this formulation | Suggested Use Level | Typical Use Levels * |
|---|---|---|---|
| Sodium Hydroxide | Sodium hydroxide is an inorganic base that is used as a pH Adjuster in personal care formulations. | not listed | CIR report: ≤10% |

* Cosmetic Use: The Cosmetic Ingredient Review (CR) Expert Panel assesses the safety of cosmetic ingredients based on the expected use of these ingredients in cosmetics. The Panel reviews data received from the U.S. Food and Drug Administration (FDA) and the cosmetics industry to determine the expected cosmetic use. The FDA collects data from manufacturers on the use of individual ingredients in cosmetics, by cosmetic product category, through the FDA Voluntary Cosmetic Registration Program (VCRP). Data from the cosmetic industry are submitted in response to a survey of the maximum reported use concentrations, by category, conducted by the Personal Care Products Council.

Methods

In another embodiment, a method for skin rejuvenation and defense is disclosed. The method for skin rejuvenation and defense includes (1) applying the skin rejuvenation application to a selected skin area, (2) leaving the skin rejuvenation application in contact with the skin for a selected period of time (e.g., about 30 seconds to about 10 minutes), (3) rinsing the skin rejuvenation application off of the skin, and (4) applying the skin defense application to the selected skin area. In one aspect, the skin rejuvenation application and the skin defense application may be applied to the selected skin area at night (e.g., before going to bed). In one embodiment, the method further includes reapplying the skin defense application to the selected skin are at least one additional time in a following 24 hour period (e.g., within 6-10 hours or after waking in the morning).

In an embodiment, the skin rejuvenation application and the skin defense application are specifically formulated to be applied to the skin of the face and neck area. Nevertheless, the skin rejuvenation application and the skin defense application can be applied to other areas such as, but not limited to, the backs of the hands, arms, and legs.

Experimental Results

A combined efficacy test and user trial was conducted with a combination treatment of the present disclosure. 30 trial participants (females between the ages of 35-64 (average 47.3) years old) were each treated over a 28-day period with a skin rejuvenation application and a skin defense application of the present disclosure. Participants washed the inner side of forearms and face and neck areas (i) twice daily with a skin cleanser, (ii) once daily (days 0-3) or once every other day (days 4-28) with skin rejuvenation application, and (iii) twice daily with skin defense application. Results were recorded 30 minutes after the initial application and after both 14 and 28 days of regular use.

For the skin cleanser, a generous amount of cleanser was applied onto wet, clean hands, massaged into face and neck and designated forearm, rinsed thoroughly with warm water (the untreated forearm was only rinsed), and patted dry with soft paper towels.

For the skin rejuvenation application, 3-6 pumps of product (A) were dispensed onto fingertips and applied to (spread quickly onto) the face and neck and designated forearm areas in quick circular motions for several seconds (without rubbing into the skin as with a moisturizer). Indicative product bubbling was noted. The product was left on the skin for at least 5, maximum 7, minutes, rinsed thoroughly with warm water (the untreated forearm was only rinsed), and patted dry with soft paper towels.

For the skin defense application, a pea-sized amount of product (B) was applied onto the face and neck and designated forearm areas and gently massaged into the skin. No rinsing or pat-drying was performed. The untreated forearm was not treated.

Measurements to study the short-term effects of the foregoing treatment on skin hydration, wrinkle depth, and skin tone evenness (lightness measurements across the face) were taken 30 minutes after application. Additional measurements on all studied parameters to study the effects of the treatment in regular use were performed after both 14 and 28 days of regular treatment 8-12 hours following the last respective application (evening before the visit). At the final visit to the test institute after 28 days of product use, the subjects were additionally asked to complete the study questionnaire, after inspecting their appearance in front of an illuminated cosmetic mirror, on their subjective assessment of the test product's efficacy.

Skin Hydration

The combination treatment was found to statistically significantly increase skin hydration in both the short-term and in conditions of regular use. Evaluated were changes in the hydration values in the treated condition (inner sides of forearms) in comparison to the changes in the untreated condition. 30 minutes after the initial product application and after both 14 and 28 days of regular use, a statistically significant ($p<0.05$) increase in skin hydration was observed in the product treated test condition as compared to the changes in the untreated condition. 30 minutes after the initial application, a mean increase of about 60% was observed and a positive effect was detected in 100% of the volunteers. After 14 days of regular use, a mean increase of about 30% was observed, and after 28 days of regular use, a mean increase of about 35% was observed and a positive effect of the test product was detected in 100% of the volunteers.

Biomechanical Properties of the Skin (Skin Firmness/Skin Elasticity)

The combination treatment was found to statistically significantly enhance the biomechanical properties of the skin towards the firm-elastic optimum in conditions of regular use. In assessing skin firmness, evaluated were changes in the parameter F4 in the treated condition (inner sides of forearms) in comparison to the changes in the untreated condition. After both 14 and 28 days of treatment, a statistically significant ($p<0.05$) decrease in F4 was observed in the product treated condition as compared to the changes in the untreated condition. The combination treatment was found to statistically significantly increase skin firmness by about 6% after 14 days of regular use and by about 15% after 28 days of regular use. After 28 days, a positive effect could be detected in 90% of the study participants.

In assessing skin elasticity, evaluated were the changes in the fraction F3 divided by F4 in the treated condition (inner sides of forearms) in comparison to the changes in the untreated condition. After both 14 and 28 days of treatment, a statistically significant ($p<0.05$) increase in F3/F4 was observed in the product treated condition as compared to the changes in the untreated condition. The combination treatment was found to statistically significantly increase skin elasticity by about 7% after 14 days of regular use and by about 10% after 28 days of regular use. After 28 days, a positive effect could be detected in 80% of the study participants. Accordingly, overall, the treatment induced a change in the biomechanical properties of the skin towards the firm-elastic optimum.

Pore Refinement

The combination treatment was found to statistically significantly refine the pores in the treatment area (to decrease roughness in an area with dilated pores) in conditions of regular use. Evaluated were the changes in the parameter Rz (roughness) as measured on the silicon imprints made from an area with dilated pores as compared to the initial condition. After both 14 and 28 days of treatment, a statistically significant ($p<0.05$) decrease in $R_z$ was observed in the product treated condition as compared to the initial condition. The combination treatment was found to statistically significantly refine the pores in the treatment area by about 8% after 14 days of regular use and by about 10% after 28 days of regular use. After 28 days, a positive effect could be detected in 80% of the study participants.

Wrinkle Depth

The combination treatment was found to statistically significantly decrease wrinkle depth in both the short-term and in conditions of regular use. Evaluated was the parameter $R_{max}$ in comparison to the initial condition. 30 minutes after the initial product application and after both 14 and 28 days of regular use, a statistically significant ($p<0.05$) decrease in $R_{max}$ was observed in the product treated condition as compared to the initial condition. The combination treatment was found to statistically significantly decrease wrinkle depth by about 6% after 30 minutes, by about 8% after 14 days of regular use, and by about 14% after 28 days of regular use. 30 minutes after the initial application a positive effect could be detected in 83% of the study participants. After 28 days, a positive effect could be detected in 97% of the study participants.

Skin Tone Evenness/Homogeneity

The combination treatment was found to statistically significantly improve skin tone evenness in the face, i.e. to improve skin tone homogeneity, in conditions of regular use. Skin tone evenness/homogeneity was assessed using the standard deviation of six skin lightness (L*) measurements made in selected spots across the face (forehead left/right, temple left/right, cheek left/right). Evaluated were the changes in the standard deviation as compared to the initial condition. After both 14 and 28 days of treatment, a statistically significant ($p<0.05$) decrease in the standard deviation of the six L* measurement repetitions could be observed as compared to the initial condition. In the short-term, 30 minutes after the initial product application, no significant changes could be detected. However, the combination treatment was found to statistically significantly improve skin tone evenness in the face in regular use, i.e. to improve skin tone homogeneity. After 28 days, a positive effect was detected in 67% of the study participants.

Subjective Evaluation (Questionnaire)

After 28 days of regular use, the majority of participants recognized an improvement in skin hydration and visual benefits as a result of the treatment.

An evaluation of the efficacy in affecting the natural skin repair process after SDS-induced skin irritation was also conducted with a combination treatment of the present disclosure. 30 trial participants (18 females, 12 males, all between the ages of 25-59 (average 39.0) years old) were each treated twice daily over a 7-day period with a skin defense application of the present disclosure. The test product was found to have a small, yet statistically significant, regeneration effect against the damaging properties of the surfactant Sodium Dodecyl Sulfate (SDS), and was found to enhance recovery from induced barrier damage and skin redness.

Phase I—Induction of Irritation

The first measurements (skin redness, TEWL) were taken after a 1 week pre-conditioning phase before any treatment (day 0—start) and subsequently, to be able to study the regenerative properties of the test product, skin irritation on the inner sides of the forearms was induced in the test areas by 1 week of twice daily washing of the forearms with 5% SDS (purity: 99%) in distilled water. After the initial washing under supervision of testing staff to demonstrate the correct procedure (application of 5 ml SDS solution per forearm by a disposable syringe, 1 minute of massaging the solution into the skin, 5 minutes of waiting, thorough rinsing with luke-warm tap water, drying with soft paper towels), the subjects performed the SDS washing twice daily (morning & evening) at home. Approximately 6 hours after the last SDS washing (in the morning of day 7), skin redness and in trans-epidermal water loss (TEWL) were recorded (day 7—after SDS).

Phase II—Evaluation of Regenerative Product Properties

After the measurements, the test product was applied for the first time (randomized location on the inner sides of the forearms) by testing staff (approximately 2 mg/cm$^2$) to demonstrate the correct product application procedure; one additional area was left untreated and served as control. On the following days, to study the effect of the product treatment on the recovery process of the skin, home application took place (twice daily in the morning & evening) and additional measurements were taken on days 8, 9, 11, and 14 (after 1, 2, 4, and 7 days of treatment respectively) in the afternoon approximately 6 hours after the respective last product use.

The solution of 5% SDS in water induced in most of the subjects after 1 week of washing measurable and overall statistically significant skin reddening in both test areas. Some of the volunteers, however, reacted with a whitening response towards the surfactant. During the following application phase, skin redness (a*) was found to decrease in both the untreated and product treated test area. The decrease in the product treated test area was found to be statistically significantly larger on days 8 and 9 (after 1 and 2 day of regular treatment) as compared to the changes in the untreated control area with "day 7—after SDS" taken as baseline (p<0.05). On day 11 (product treated area and untreated control area), skin redness was found (in statistical terms, p<0.05) to have returned to its original level. Thus, the test product was found to have a small, yet statistically significant, regeneration effect on skin redness induced by the damaging properties of the surfactant SDS as evidenced by the statistically significantly larger decrease in redness on days 8 and 9 (i.e. to enhance recovery from induced skin redness).

The solution of 5% SDS in water also induced in all subjects after 1 week of washing a measurable and overall statistically significant increase in TEWL in both test areas. During the following application phase, TEWL was found to decrease in both the untreated and product treated test area over time. The decrease in the product treated test area was found to be statistically significant larger on day 9 (after 2 days of regular treatment) as compared to the changes in the untreated control area with "day 7—after SDS" taken as baseline (p<0.05). On day 14 (test product treated area & untreated control area), TEWL was found (in statistical terms, p<0.05) to have returned to its original level. Thus, the test product was found to have a small, yet statistically significant, regeneration effect against the damaging properties of the surfactant SDS with regards to its effect on the barrier function of the skin as evidenced by the statistically significantly larger decrease in TEWL on day 9 (i.e. to enhance recovery from barrier damage).

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems, processes, and/or products according to certain embodiments of the present disclosure may include, incorporate, or otherwise comprise properties features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features without necessarily departing from the scope of the present disclosure. Moreover, unless a feature is described as requiring another feature in combination therewith, any feature herein may be combined with any other feature of a same or different embodiment disclosed herein. Furthermore, various well-known aspects of illustrative systems, processes, products, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. A method for skin rejuvenation and defense, comprising:
    applying a skin rejuvenation application to a selected skin area, wherein the skin rejuvenation application includes:
        a *Coenochloris signiensis* (Snow Algae) preparation;
        *Leucojum aestivum* bulb extract;
        perfluorocarbons, comprising perfluorohexane, perfluorodecalin, and pentafluoropropane; and
        water;
    leaving the skin rejuvenation application in contact with the skin for a selected period of time;
    rinsing the skin rejuvenation application off of the skin; and
    applying a skin defense application to the selected skin area, wherein the skin defense application includes:
        *Taraxacum officinale* (dandelion) extract;
        a pre-/pro-biotic complex, comprising alpha-glucan oligosaccharide, β-fructooligosaccharides, maltodextrin, and *Lactobacillus* sp. bacteria;
        an emulsifier;
        a moisturizer; and
        water.

2. The method of claim 1, wherein the skin rejuvenation application and the skin defense application are applied to the selected skin area at night, and the method further comprises reapplying the skin defense application to the selected skin area at least one additional time in a following 24 hour period.

3. The method of claim 2, wherein the skin defense application is reapplied to the selected skin area at least once within a period of 6-10 hours after the first application.

4. The method of claim 1, wherein the selected skin area includes at least a portion of a human face.

5. The method of claim 4, wherein the selected skin area includes skin of the face and neck area.

6. The method of claim 1, wherein the selected period of time that the skin rejuvenation application is in contact with the selected skin area ranges from about 30 seconds to about 10 minutes.

7. The method of claim 1, wherein the method includes dispensing an amount of the skin rejuvenation application sufficient for a single application from an airtight container.

8. The method of claim 1, wherein the emulsifier and the moisturizer of the skin defense application comprises butylene glycol, shea butter, hydroxyethyl urea, propanediol, a gelling agent comprising sodium acrylates copolymer and lecithin, and an emulsifying agent comprising polyglyceryl-6 distearate, jojoba esters, polyglyceryl-3 beeswax, and/or cetyl alcohol.

9. The method of claim 8, wherein the skin defense application includes about 1-5 weight % (wt %) of the *Taraxacum officinale* extract, about 1-5 wt % of the pre-/pro-biotic complex, about 3-10 wt % of the butylene glycol, about 0.1-3 wt % of the shea butter, about 0.1-3 wt % of the hydroxyethyl urea, about 0.1-3 wt % of the propanediol, about 0.1-3 wt % of the gelling agent, about 1-5 wt % of the emulsifying agent, and about 60-80 wt % water.

10. The method of claim 1, wherein the skin rejuvenation application comprises a blend of water, acrylates copolymer, DL-Panthenol, hydroxyethyl urea, pentylene glycol, decyl glucoside, sodium lauroyl methyl isethionate, cocamidopropyl betaine, sodium methyl oleoyl, taurate, sodium cocoyl isethionate, *Leucojum aestivum* bulb extract, maltodextrin, *Coenochloris signiensis* extract, lecithin, propanediol, xanthan gum, aminomethyl propanol, ethoxydiglycol, polysorbate 20, phenoxyethanol, caprylyl glycol, ethylhexylglycerin, hexylene glycol, caprylic/capric triglyceride, *Citrus aurantium dulcis* (orange) fruit extract, *Citrus aurantium dulcis* (orange) peel extract, *Lavandula angustifolia* (Lavender) flower/leaf/stem extract, *Elettaria cardamomum* seed extract, *Gardenia taitensis* flower extract, *Prunus armeniaca* (apricot) fruit extract, *Pyrus malus* (apple) fruit extract, *Hibiscus Abelmoschus* seed extract, *Eugenia caryophyllus* (clove) flower extract, *Vanilla planifolia* fruit extract, *Jasminum officinale* (jasmine) flower/leaf extract, *Hedychium spicatum* extract, *Plumeria rubra* flower extract, perfluorohexane, perfluorodecalin, and pentafluoropropane.

11. The method of claim 1, wherein the skin defense application further comprises tetrasodium glutamate diacetate, acrylates/C10-30 alkyl acrylate crosspolymer, dimethicone, phenoxyethanol, decylene glycol, 1,2-hexanediol, caprylyl glycol, sodium pyrrolidone carbonic acid (PCA), a Vitamin E blend, hydrolyzed Jojoba esters, allantoin, and an aromatic Ginger Yuzu extract blend, and, optionally, citric acid and/or sodium hydroxide to a pH of about 5.75-6.25.

12. The method of claim 1, further comprising applying a skin cleanser to the selected skin area prior to application of the skin rejuvenation application.

13. A method for skin rejuvenation and defense, comprising:
applying a skin rejuvenation application to an area of skin, the skin rejuvenation application comprising:
a *Coenochloris signiensis* (Snow Algae) preparation;
*Leucojum aestivum* bulb extract;
perfluorocarbons, comprising perfluorohexane, perfluorodecalin, and pentafluoropropane; and
water;
leaving the skin rejuvenation application in contact with the area of skin for a selected period of time;
rinsing the skin rejuvenation application off of the area of skin; and
applying a skin defense application to the area of skin after rinsing the skin rejuvenation application off of the selected area of skin, the skin defense application comprising:
*Taraxacum officinale* (dandelion) extract;
a pre-/pro-biotic complex, comprising alpha-glucan oligosaccharide, β-fructooligosaccharides, maltodextrin, and *Lactobacillus* sp. bacteria;
an emulsifier;
a moisturizer; and
water.

14. A method for skin rejuvenation and defense, comprising:
applying a skin rejuvenation application to a selected skin area, wherein the skin rejuvenation application includes:
a *Coenochloris signiensis* (Snow Algae) preparation;
*Leucojum aestivum* bulb extract;
perfluorcarbons, comprising perfluorohexane, perfluorodecalin, and pentafluoropropane; and
water;
leaving the skin rejuvenation application in contact with the skin for a selected period of time;
rinsing the skin rejuvenation application off of the skin; and
applying a skin defense application to the selected skin area, wherein the skin defense application includes:
about 1-5 weight % (wt %) of *Taraxacum officinale* (dandelion) extract;
about 1-5 wt % of a pre-/pro-biotic complex, comprising alpha-glucan oligosaccharide, β-fructooligosaccharides, maltodextrin, and *Lactobacillus* sp. bacteria;
about 3-10 wt % of butylene glycol;
about 0.1-3 wt % of *Butyrospermum parkii* (Shea) butter;
about 0.1-3 wt % of hydroxyethyl urea;
about 0.1-3 wt % of propanediol;
about 0.1-3 wt % of a gelling agent, comprising sodium acrylates copolymer and lecithin;
about 1-5 wt % of an emulsifying agent, comprising polyglyceryl-6 distearate, jojoba esters, polyglyceryl-3 beeswax, and cetyl alcohol; and
about 60-80 wt % water.

15. The method of claim 14, wherein the skin rejuvenation application and the skin defense application are applied to the selected skin area at night, and the method further comprises reapplying the skin defense application to the selected skin area at least one additional time in a following 24 hour period or within a period of 6-10 hours after the first application.

16. The method of claim 14, wherein the selected period of time that the skin rejuvenation application is in contact with the selected skin area ranges from about 30 seconds to about 10 minutes.

17. The method of claim 14, wherein the skin rejuvenation application comprises a blend of water, acrylates copolymer, DL-Panthenol, hydroxyethyl urea, pentylene glycol, decyl glucoside, sodium lauroyl methyl isethionate, cocamidopropyl betaine, sodium methyl oleoyl, taurate, sodium cocoyl isethionate, *Leucojum aestivum* bulb extract, maltodextrin, *Coenochloris signiensis* extract, lecithin, propanediol, xanthan gum, aminomethyl propanol, ethoxydiglycol, polysorbate 20, phenoxyethanol, caprylyl glycol, ethylhexylglycerin, hexylene glycol, caprylic/capric triglyceride, *Citrus aurantium dulcis* (orange) fruit extract, *Citrus aurantium dulcis* (orange) peel extract, *Lavandula angustifolia* (Lavender) flower/leaf/stem extract, *Elettaria cardamomum* seed extract, *Gardenia taitensis* flower extract, *Prunus armeniaca* (apricot) fruit extract, *Pyrus malus* (apple) fruit extract, *Hibiscus Abelmoschus* seed extract, *Eugenia caryophyllus* (clove) flower extract, *Vanilla planifolia* fruit extract, *Jasminum officinale* (jasmine) flower/leaf extract, *Hedychium spicatum* extract, *Plumeria rubra* flower extract, perfluorohexane, perfluorodecalin, and pentafluoropropane.

18. The method of claim 14, wherein the skin defense application further comprises tetrasodium glutamate diacetate, acrylates/C10-30 alkyl acrylate crosspolymer, dimethicone, phenoxyethanol, decylene glycol, 1,2-hexanediol, caprylyl glycol, sodium pyrrolidone carbonic acid (PCA), a Vitamin E blend, hydrolyzed Jojoba esters, allantoin, and an aromatic Ginger Yuzu extract blend, and, optionally, citric acid and/or sodium hydroxide to a pH of about 5.75-6.25.

19. A method for skin defense, comprising:
  applying a skin defense application to a selected skin area, wherein the skin defense application includes:
    about 1-5 weight % (wt %) of *Taraxacum officinale* (dandelion) extract;
    about 1-5 wt % of a pre-/pro-biotic complex, comprising alpha-glucan oligosaccharide, β-fructooligosaccharides, maltodextrin, and *Lactobacillus* sp. bacteria;
    about 3-10 wt % of butylene glycol;
    about 0.1-3 wt % of *Butyrospermum parkii* (Shea) butter;
    about 0.1-3 wt % of hydroxyethyl urea;
    about 0.1-3 wt % of propanediol;
    about 0.1-3 wt % of a gelling agent, comprising sodium acrylates copolymer and lecithin;
    about 1-5 wt % of an emulsifying agent, comprising polyglyceryl-6 distearate, jojoba esters, polyglyceryl-3 beeswax, and cetyl alcohol; and
    about 60-80 wt % water.

* * * * *